US012606875B2

(12) United States Patent
Nylund et al.

(10) Patent No.: US 12,606,875 B2
(45) Date of Patent: Apr. 21, 2026

(54) FISH TOTIVIRUS

(71) Applicant: Pharmaq AS, Overhalla (NO)

(72) Inventors: Stian Nylund, Strusshamn (NO); Liv Sandlund, Loddefjord (NO); Arnfinn L. Okland, Erdal (NO)

(73) Assignee: Pharmaq AS, Overhalla (NO)

( * ) Notice: Subject to any disclaimer, the term of this patent is extended or adjusted under 35 U.S.C. 154(b) by 991 days.

(21) Appl. No.: 17/433,416

(22) PCT Filed: Feb. 4, 2020

(86) PCT No.: PCT/EP2020/052683

§ 371 (c)(1),
(2) Date: Aug. 24, 2021

(87) PCT Pub. No.: WO2020/161105

PCT Pub. Date: Aug. 13, 2020

(65) Prior Publication Data

US 2025/0270661 A1 Aug. 28, 2025

(30) Foreign Application Priority Data

Feb. 5, 2019 (EP) .................................... 19155628

(51) Int. Cl.

| | |
|---|---|
| *C07K 14/005* | (2006.01) |
| *A61K 39/12* | (2006.01) |
| *C07K 14/08* | (2006.01) |
| *C07K 14/165* | (2006.01) |
| *C07K 16/08* | (2006.01) |
| *C07K 16/10* | (2006.01) |
| *C12N 7/00* | (2006.01) |
| *C12N 15/113* | (2010.01) |
| *C12Q 1/686* | (2018.01) |
| *C12Q 1/6869* | (2018.01) |
| *C12Q 1/70* | (2006.01) |

(52) U.S. Cl.
CPC .............. *C12Q 1/701* (2013.01); *A61K 39/12* (2013.01); *C07K 14/005* (2013.01); *C07K 16/10* (2013.01); *C12N 7/00* (2013.01); *C12N 15/1131* (2013.01); *C12Q 1/686* (2013.01); *C12Q 1/6869* (2013.01); *C12N 2310/14* (2013.01); *C12N 2720/00021* (2013.01); *C12N 2720/00022* (2013.01); *C12N 2720/00034* (2013.01)

(58) Field of Classification Search
CPC .... C07K 14/005; C07K 14/08; C07K 14/165; C12N 7/00; C12N 2770/20021
See application file for complete search history.

(56) References Cited

U.S. PATENT DOCUMENTS

| | | |
|---|---|---|
| 9,551,009 B2 | 1/2017 | Fontayne et al. |
| 2003/0165831 A1 | 9/2003 | Lee et al. |
| 2009/0062131 A1 | 3/2009 | Mounts |
| 2013/0129668 A1 | 5/2013 | Firestein et al. |
| 2016/0078168 A1 | 3/2016 | Zhuo et al. |

FOREIGN PATENT DOCUMENTS

| | | |
|---|---|---|
| CN | 107119046 A | 9/2017 |
| EP | 2834260 A1 | 2/2015 |
| WO | 2011131600 A1 | 10/2011 |
| WO | 2013033627 A2 | 3/2013 |
| WO | 2018224516 A1 | 12/2018 |

OTHER PUBLICATIONS

Affymetrix Inc: Geneseq, Jul. 7, 2011, Database accession No. 2011166037.202956, XP002792400.
Altschul, et al., Methods in Enzymology, 1996, vol. 266, pp. 460-480.
Altschul, et al., Nucleic Acids Research, 1997, vol. 25, pp. 3389-3402.
Altschul S.F., et al., "Basic Local Alignment Search Tool," Journal of Molecular Biology, 1990, vol. 215, pp. 403-410(8 Pages).
Bates, et al., Biotechniques, 2006, vol. 40, No. 2, pp. 199-208.
Clem, et al., Virology Journal, 2007, vol. 4.
Database Embl: "GHMBLKH02B753Scounts=4 Transposon Integration Site Library in HEK293 Homo Sapiens Genomic, Genomic Survey Sequence," EBI accession No. Em GSS:JS760174 Database accession No. JS760174 sequence, Jan. 26, 2012, XP002792404.
Database Geneseq: "Human Derived Single Nucleotide Polymorphism Comprising Dna Seq ID:5084," EBI accession No. GSN:AYC48348 Database accession No. AYC48348 sequence, Aug. 5, 2010, XP002792403.
Database Geneseq: "Human Microarray DNA Oligonucleotide Seq Id No 58477," EBI accession No. Gsn: ACI58486 Database accession No. ACI58486 sequence, Oct. 13, 2003, XP002792402.
Devereux J., et al., "A Comprehensive Set of Sequence Analysis Programs fro the VAX," Nucleic Acids Research, 1984, vol. 12, No. 1, pp. 387-395.
Expert Review on Vaccines, 2005, vol. 4, No. 1, pp. 89-101.
Extended European Search Report for European Application No. 19155628.1, mailed Jul. 12, 2019, 12 Pages.
Feng, et al., Journal of Molecular Evolution, 1987, vol. 35, pp. 351-360.
Gardner S., et al., Database Accession No. U.S. Pat. No. 2013267429. 326146, Database Geneseq, abstract, sequence, Oct. 10, 2013, XP002792401.
Goodwin S., et al., "Coming of Age: Ten Years of Next-Generation Sequencing Technologies," Nature Reviews Genetics, 2016, vol. 17, pp. 333-351, DOI: 10.1038/nrg.2016.49, XP055544186.
Gribskov, et al., Nucleic Acids Research, 1986, vol. 14, p. 6745.
Gudmundsdottir S., et al., "Outbreak of Viral Haemorrhagic Septicaemia (VHS) in Lumpfish (Cyclopterus Lumpus) in Iceland Caused by VHS Virus Genotype IV," Jouranl of Fish Disease, 2019, vol. 42, pp. 47-62.
Haugland O., et al., "Cardiomyopathy Syndrome of Atlantic Salmon (Salmo Salar L.) Is Caused by a Double- Stranded RNA Virus of the Totiviridae Family," Journal of Virology, Jun. 2011, vol. 85, No. 11, pp. 5275-5286.

(Continued)

*Primary Examiner* — Barry A Chestnut
(74) *Attorney, Agent, or Firm* — Vyacheslav Vasilyev

(57) ABSTRACT

The invention relates to a novel fish virus, indicated to be a Totivirus, which causes mortality in fish, and to methods of detecting said virus in fish, and related uses.

22 Claims, 14 Drawing Sheets

Specification includes a Sequence Listing.

(56) References Cited

OTHER PUBLICATIONS

Higgins D.G., et al., "Fast And Sensitive Multiple Sequence Alignments On A Microcomputer," Cabios Communications, 1989, vol. 5, No. 2, pp. 151-153(4 Pages).

International Preliminary Report on Patentability for International Application No. PCT/EP2020/052683, dated May 6, 2021, 23 Pages.

International Search Report and Written Opinion for International Application No. PCT/EP2020/052683, dated Mar. 11, 2020, 20 Pages.

Karlin, S. et al., "Applications and statistics for multiple high-scoring segments in molecular sequences," Proceedings of the National Academy of Sciences U.S.A., vol. 90, pp. 5873-5877, Jun. 1993.

Kibenge M.J.T., et al., "Whole-Genome Analysis of Piscine Reovirus (PRV) Shows PRV Represents a New Genus in Family Reoviridae and its Genome Segment Si Sequences Group it into Two Separate Sub-Genotypes," Virology Journal, 2013, vol. 10, No. 230, 20 Pages.

Kongtorp R.T., et al., "Heart and Skeletal Muscle Inflammation in Atlantic Salmon, Salmo Salar L.: A New Infectious Disease," Journal of Fish Diseases, 2004, vol. 27, pp. 351-358.

Needleman, et al., Journal of Molecular Biology, 1970, vol. 48, p. 443.

Pearsonlipman, Proceedings of the National Academy of Sciences of the United States of America, 1988, vol. 85, pp. 2444-2448.

Sandlund L., et al., "Comparative Molecular Characterization of Novel and Known Piscine Toti-Like Viruses", Viruses, vol. 13, No. 6, Article 1063, Jun. 3, 2021, pp. 1-20.

Skoge R.H., et al., "New Virus of the Family Flaviviridae Detected in Lumpfish (Cyclopterus Lumpus)," Archives of Virology, 2018, vol. 163, pp. 679-685.

Smith, et al., Advances in Applied Mathematics, 1981, vol. 2, p. 482.

Tang, et al., Nature, 1992, vol. 356, No. 6365, pp. 152-154.

Tighe, et al., Immunology Today, 1998, vol. 19, No. 2, pp. 89-97.

CLuTV_ Genome nucleotide sequence  (Seq. ID No.: 6)

AGAAGAATTACCACAGGATACGTCTGGCATTCAGAGTTATTGCCCACTGGGTTATTCACTCTGAACTTTTGGAAGTAGGAGGAGGGTATACAGTCTGGAGAAATTGAAGAATGACCCTC

GTGACCGGGATGCGGAGTGGGAGTTCTGTTACACCTTAAGAGTTCATGGGAGAATGGCTAACTCTTCAGGCAGAAGATCAGGATGATAGTTACTCTTTCAAAAACCACACCAGT

TGACCTTTGCACTGGAAGAGCAGGGTGTGGCTAATGTCATAGTTCAACTAGATGTCATAGTTCAACATTTCAACACCATGAAGAGGTAACTAGTTCAACATTTCAGTTGGTTCAGTTTCTACTC

ACTCTCGGTAAATATGTCGATAAAGAATTATTGTACAACAGTACCTCGACTTGGAAATTACCAGGAATACCAGGTGAAATGGTGAAATCTTGAC

CTTTTTGGTCTGCAGAGGTTGAAGGAAAGAAGAAGAGTCATTAATGCAATGACAATGGAATGTCTCAATTAATTCTCTCTTATAGAGAGGCACAGCATCACACAACACACACTCA

CACACACCAACGCACACACTAGGCTGGCGGGCCCTATAGGAGTACCCCTGACTCCGAATATAAAATCTAATGGGGGCCTGTAGTTAAGCAC

FIG. 2C

CLuTV_ORF-1    (Seq. ID No.: 1)

ATGGACGGCAAACAAACAAGAAACACAAATAACAGAGGAGAAAGTAGAGAGGAGGAGGAGGTTACCTTACAGGTGGAAGTAAGGAGGAAGATACGGGATTACTCCAAGACCCAACGAGTAAAGA
AGCCCCTGACAAAACTGATCACCGACCTAGCCAAAAAAACAAAGGGAGGTGGTCTCTGATGCAACCGATTTCGGGGTTGGACATGCCAACAACTCTACAGTCAAGACAGTCAAACAGTC
AGTTCCACGTGTTGAGGAAGGAAATGTAGATACCAGGATAGCAGCATCGGAGAGAGGATCAACACACACACAAGAAGGCTTGCCACTATTGGTAACGTGGAGCCATGCTGGTTCAGA
ACAGGACCGGGGTGTTAGGGGGGGGGGGGATATTGATTGAACCCTCAAACGCTGTTCTGGCTCTGAAACCTCTTCCAGGGTGCAGACCCGGACCTCTTTCAAGTAGTGCGCGTTTGGA
TATTAACAACTATTCATCCATCCCAGACACGGCCCTTGGCTTCATGAACAGCATTGGAGCAGCATGGAGGTTCATTTCTGAGCCGTCGGTTGATTCGCGCCTTTCATCTTCTCAA
TTGATGATCATATAGAGGTGAATCACCCCTCTCGTGGTTGGGGAACAGAACGACGCTTTTGCCGCGCCCACTTGGTACATTACCTAGTGGGGATTACTTTCCAGCATCTGTAAGA
TCAGCTGGATGGGTGGCGGGGAGACACACAGGCTATGATTGTGAACGCTGAAGACTTTGCAAGGGAGGAGGCAAGGGCCGAGGAGAGGTTCAATGACGGTTGGGGGGCAACAGTATGGAA
TGTACCAGGAGTAGAAGGTGTGGCAGTTGTGTCCCAGACCAATCAATTCTATCTGGATGCTCATCGACACATGGAAAAATCCAATCCGTACAAGGT
TTGTTGAGGTTGATGAGGTTGACATGTTGCTGGTGATCCTCAGGTGGTTCAGAATGGGACAAATCTTCAACATCTGTTGTTCCGGACCCGTCAAAGAGAAGTTCTCTTCGTGATC
ACTGACAATGAACAACCAGAGTGGGGACATACTCCTGGACACATTCAACGGTCTCGGTCAGATTTCAACGGTGCTGTTGACAACATCGTCATAGGAGGAGTGCCGGTCTGGGAGGCTTCACTAG
ACTAATACCTGCCTGGATGGGTTCGATCCTGATCGTCGGTCAGAGTTGGGGATTGCTGGAGTTGGGGAATCACTATGCTGAGGAGAACAGGGTCAGGAGGTACAGGAGGATTGCCCAATACCCACTGAAT
CCATCGGTGAGTGAGATGCTCGTCACTTTCCCTGGACAGGTTAGCGGCTGCAGGAAGTTAGCATTAGCTGGAAGAGAGTCTGACATCATGACGTACACCAGCTTCGGGCTACAGGCGATCAAACAA
GGTATTGATGTGGTGTTGTATGATGGGTTCGGTTTCCTATACTGTCGGTTTCCTCAGAAGCAGCCGTGGCTGTAAGTGCTCTACTCTATAAGCCTATAAGACCATCGGAAATGAGTTGA
TCCAAACACTTCGCCTCCAATGCTCCCATTCGCCTCCTATACTGTCGGTTTCCTCAGAAGCAGCCGTGGCTGTAAGTGCTCTACTCTATAAGCCTATAAGACCATCGGAAATGAGTTGA
GACCTGCCATCCTGGCTGATAACATCTACAGGAGAAGAGAAACAGCAGTCATGGTGGACATCATCGCAGGCCAGATAGGTGCAGTTTCTAGGATGACCAACACCCCAGGGAAC
TCAGAACAACAAGGTCAGATTGCATGGAGAGAAACCTTTACACGGATGGCCGTCAGGGTACCACGGATGCGCAGGGTACCACGGATCTGCTGGGATTTGATGGAAGGATGG
TAACCAACAAGGTCAGATTGCATGGAGAGAAACCTTTACACGGATGGCCGTCAGGGTACCACGGATGCGCAGGGTACCACGGATCTGCTGGGATTTGATGGAAGGATGG
AAATCGATGACCTCTACAACTTCAAAACAGAGGGATTCGACGACGTGGATGGGCGCCACTTGACATTGGAAAACTCCACATCAAAGGAGGACGGACAGGTC
ACCGGCACGAAGGCTGACTTCAGCAGCAGGAAGGAAGGAAGTAAGATATTCCAACTATGGATTTGTACCACTCGTAAGGGCTAACGGAGCAGAGTTCGGCACCACTGGTCACACAGGTCACACAGAACGATG
AAACCCAACACAGTTGGAAGAGGAAGGAAGGAAGTAAGATATTCCAACTATGGATTTGTACCACTCGTAAGGGCTAACGGAGCAGAGTTCGGCACCACTGGTCACACAGGTACCTTCACAGAACGATG
CCAATCACATCATTCACCCTGCAGTTCGCGGTTGGAAGGCCTCGGTGTTAGGAAACATGGAAATGTTCAATCACTTCAATCCAATCCAGAAT
CCCACAACCGACACACAGACCGTGAACAACGCCACCGTCCTGGATTTC

FIG. 3

CLuTV_ORF-2  (Seq. ID No.: 2)

ATGACACAATTTAATCAATTTATTAGAGAAAACAAACTTGACCCATCAAAGGTGTTCAAAAATTTAACAACACAGGTAAAGTTGGCTGGTGTGAGGGATTCAGTAGTGACTGGAGGTA

TTATGTGAACTGGGAATTACTTGGTGGTGGATCTCCGAGGAACACCGACCAGGATCCGAGGAGTAAGGGCTTTTACACACGCAGGAGAAGTCGGCAGGAGTTCGGAGGGGGCCGG

TTGTTAAAGCATTGGAAGAACTTCTTGCCCCTTTATCAGGAGTGGTACGTTCAAAGAGAGAACTTTTGGAGGAGTTCCTACTGGACAGAGAGATGCATGGGCGGAAGAATACATCAGGTTTT

GTTACAAGTAACATCAAGAAGAAAGAAGAACAAGATTGAGGTTGCAGAGAACAAGACTACTGGAGATAGTTACCTTGGAGAATATCAAACACAGGCCATTTATAAA

ACAAGAACCAGGAAAAAGCCAGGCCGGTAGTTAATTCAAACTTACCGCGCCCTACCTTTTCATGAGTTGGGTTTTCGAACAAATCGAGCCCATTTGAGGAAAAAACTTTTCATCAAAAA

CTACCATCTTCGATTCAGCATGGACACAAAGAGTGAGTTGTGGCATCAAATGACACGACGTCAGGTATAAGAAAGGAATTTTCGTTCGTCGCCTTGACTATTCGAGATTCGATTCAACA

ATTAGTAAGAACTAGCTGTGTAACAGCATTCAATATGCTAGTTGACATACTCGTCGACATCCCCTCTGATCTGCGAAGGTCAGCCAAATACAGGTTCAGGAATCAAGTGATTCTGAC

GGGTGAGGAAAGTTGGACGTTGGAACAATGCCGTTTCTTTCGGGATGGCGTTGGACTGCTCTCGATTACATCATTAGTCAATCCTAGAAGCTGCAGAGGTTACCAGAACAG

GGACGGGGATTAGAGTACAAGGGGACGGACGTGCCGTGTTTTCTTTCAAAAGAAAAGGAGATGCAGAAATTGCAATTGCGAAAATCAACTCATTCGGTTCGAAATCAACAACAAAA

GTCTTTTCTCGAAAAAGGAGAGAATGAGTATCTAAGAATGGTAGCAACGATGAATTACGTGGTCACTCCCAAAAATATTGTTGTGGGACCAACTGAAAACACT

TACCGACAGATCAGAGAAGACAGAGTAAATGGAATAGTCAACAAATGGACAACACTGGGTTGTCAAGAGGAGAAATGAGAGTAGGTGCTGGAAGATGCGTTGTTACCGATATTGCGGGTT

TAACCCAATGGTCACGTGATAACATCAAGAAGAGTGGCTTCAAACACCTTCAAACGTCACTGGGTGGTGGTGCAGGACTGTTCCAGAACAACGTCACAAGGAATTAGACTCAAAATCAAACA

GAGATTAAGGAGGAATTTGGGAACTGGGAACTTACACAAGCTGGCGAGTGATTACCGTGGGAAATTTATGGGCCAGAGGTAGGAGAACTTGGGGAAATTATGTCTGCACAATTAGA

AGAAATCCACATTCCACAGCCATTAGGAGTTGGCCAACGCTTTCATCTTTACAAGAAGAAGAGCCCACAGTTAGGTTCAAAGAAGAGAAGCATTAGGATCCACAAAACGTGACG

CCTTGATTAGGGATAAGGATTGGGATGCACTTGAGATTGGTTGAGAAGAAGTCTGAGGTATTGTTTTGGAAGAAGTAGCGTTTCTATCGTATGTTGCTTGTCGAA

GGAGGGTTTTTCAACTCCTATTCCAAAAAACAACACTCGTGAATAATGAAATAGTTGCTAGCGTCTCAGCTTTCGTAGCGTGGTATACTTTGAAAAGATCATGAAGAAGTATAATGGAATATT

GAGTGGTGAAAAGCTCCAGAGACTTCAACTTGGGGCAGAGTACTATTCAAACTTCTTACTGGACTCATTCAAACGCTTTGGTAAA

FIG. 4

CLuTV_ORF-X (Seq. ID No.: 3)

ATGGAAAATGAAAAGAACGTAAGAAGTAGGTAGTGTTACAGTGTAAGTGCTGCTGTGTTTGGATCTTACAATCTGTACAGCACAAGACACAACACTGCCAGGTGGGAGATTTGGAGGCTAAGCA

GAGCTGGGATTCACCAGTTGTGACGGCGATGATAGTGATCGGAGTCGTGGCATTCATTCTGATGGTGGTGTGGATGTTGAGAGGAGCCTGCAAGGGCTACACCGGTGTGAAGAGAC

CGCATGGGAACGAAGAGGCTCTCCAACTTCAGGACGTA

CLuTV_ORF-Y (Seq. ID No.: 4)

ATGTCAGTGATGTGGGATAACGAATGGATAAGGTTGAGTAGGGTTAGCAGGAGTTCTGTTGCCGTGAAAAGAAATATATACGGTGAACGGGTTGAACGCTTACTACTCAGCTTTGG

ATCAGAGGCTTCTGTCTTCGAATGGTTGGAGTAGAGAGGAAGAGATTACCACAGGATACGTCTGGCATTCAGAGTTATTGCCCACTGGGTTATTCACTCTGAACTTTGGAAGTAG

GAGGAGGGTATACAGTCTGGAGAAATGAAGATGACCCTCGTGACCGGGATGCGGAGTGGGAGTTCATGGGAGTTCATGGGAATGGCTAACTCTCTTCAGGCAGAGA

TCAGGA

CLuTV_ORF-Z (Seq. ID No.: 5)

ATGATAGTTTACTCTTTCAAAAACCACCACAACCAGTTGACCTTTGCACTGGAAGAGAGCAGGGTGTGGCTAATGTCATAGTTCAACTAGATGACAAGTGGAAGGAGGTAACATTTCAACA

CCATGAGAGGAAAGAGTTGGTTCAGTTTCTACTCTCTCGGTAAATATGTCGATAAAGAATTATGTACAACAGTACTCGACTTGGAAATTACCGAAGAAGATGATCTTGAGTATG

AAAAGGAATACCAGGTGAATGGTGAAATCTTGACCTTTTGGTCTGCAGAGGTTGAAGGGAAAGAAGAAGTCATTAATGCAATGACAATGGAATGTCTCAAT

FIG. 5

CLuTV_ORF-1_aa (Seq. ID No.:7)

MDANKETQITEEKVGEEVTLQVEVREEPTGLLQPTSKEALFKLITDLAKKQREVVSDAT

DFGLDIATTLQSRQSNSQFHVLREGNVDTRIASERGSTTHTRRLATIGNVEPCWFRTAPG

VRGGILIEPSNAVLALKPLFQGADPGPLSSSARLDINNYSSQTALGFMNSIGADIESNRV

SFSEPLIRAFIFSIDDHIRGESPLSWLGNRTTLLPRPLGTLPSGDYFPASVRSAGWVAGD

TQAMIVNAEDFAREARGEERFNDGWGATVWNVPGVEGVAVVPIKLADQGDPAINSIWMLM

HMENPIRTREFEVEVDEVDMLLDDPQVGSEWTNLSTSVVPGPSKKVLFVITDMNNNQSGDIL

LDDFNGAVDNIDQAANVIGGVPVDIGALIPAWMGLDFDRRSELGIAGVRRWTRYYGNTQD

WEASLAIVSEMLVTFPGQVQRSGRTGAENHYADAGGGIAQYPLNGIDVVLYDGLTAAEKL

ALAGRESDIMTTPASGYRQRSNNPNTSPPMLLYCRFSSEAAVAVSALLYKPRFTMTIGNE

LRPAILADNIYRRGKRTAVMVDIIAGQIGAVSRMTNTPGNSEQPAVAQAIVRQLAGCATR

LHQETCAGELVNITVSGWNNQQGQIAWRNLYTIGPDRTLSCRVPRMEYNSLGFDGRMEID

DLYNFKTEGFDALDIDGQQWDHMNWKTPHQKEDGQVTARRLFSAAGWTRALVPLDNIGLV

RANGAEFAPLGVHVLNPTVGRGKEVRYSNYGFVPLASEIRELFLVTQVPSQNDANHIIHP

AVRGGGRPLVLGNMGMFNPIFMDRTPGQRASQNPTTDFQTVNNATVLDF

FIG. 6

CLuTV_ORF-2_aa  (Seq. ID No.: 8)

MTILINFIRENKLDPSKVFKNLFNKVKLLAGEGFSSDWRYYVNWELLGGYQDLEEHDMIEE

VPRAFTTQEAKSAEFGGPVVKALEELLAPLSGVVRSKRTLEEFLLDRDAWAKNTSGFVTSN

IKKGKNKIEVAENMDIKELLEIVYLGEYQNRPFIKQEPGKARPVVNSNLPPYLFMSWVFE

QIEPFLRKNFSSKTTIFDSAWTKSELMHQMTDDVRYKKGIFVPLDYSRFDSTISKELAVT

AFNMLVDILVDIPSDLRRSAKYRFRNQVILTGEESWTWNNAVLSGWRWTALITSLVNLAI

LEAAEVTRTGTGIRVQGDDVRVFFQKKGDAEIAIAKINSFGFEINPTKVFCSKRRDEYLR

MVATDELRGYPIRSLFKILFVGFTETHTDRSEDRVNGIVNKWTTLVSRGGNESRCWKMLV

TDIAGLTQWSRDNTKKWLQTPSALGGAGLFQNTTSQGIFLRKTEIKEDLGTYKLASDYP

GDLGNLWARGRNSKSKLLSAQLEEIHIPQPLGVWPNAFIETKKKKPTVRFKEEALGSTKR

DALIRDKDWDALEDLVENKSEVLFWKRVLPRFFYRMLLVEGGFSTPIPKTLVNNEIVATV

SAFVAWYTFEKIMKYNGILSGERLQRLQLGAEYYSRFLLDSFKRFGK

FIG.7

CLuTV_ORF-X_aa (Seq. ID No.: 9)

MENEKNVRVGSCYSVSAVFGSTICFAQRNTAGGDLRAKQSWDSPVVTAMIVIGVVAFILM

VVWMLRGACKGYTVVKRPHGNEEALQLQDV

CLuTV_ORF-Y_aa (Seq. ID No.: 10)

MSVMWDNEWIRLSRVSRSSVAVKRNIYGERVERLLLSFGSEASVFEWFGVEEEDYHRIRL

AFRVLAHWVIHSELLEVGGGYTVWRNEDDPRDRDAEWEFCYTLRVHGRMANSSGRRSG

CLuTV_ORF-Z_aa (Seq. ID No.: 11)

MIVYSFKNHNQLTFALEEQGVANVIVQLDDKWKEVTFQHHERKELVQFLLTLGKYVDKEL

CTTVLDLEITEEDDLEYEKEYQVNGEILTFWSAEVEGKEVINAMTMEMECLN

FIG. 8

SEQUENCE LISTING

```
<160> NUMBER OF SEQ ID NOS: 49

<210> SEQ ID NO 1
<211> LENGTH: 2484
<212> TYPE: DNA
<213> ORGANISM: Unknown
<220> FEATURE:
<223> OTHER INFORMATION: Fish totivirus ORF-1 nucleotide sequence

<400> SEQUENCE: 1
atggacgcaa  acaaagaaac  acaaataaca  gaggagaaag  taggagagga  ggttacctta        60
caggtggaag  taagggagga  agatacggga  ttactccaag  acccaacgag  taaagaagcc       120
ctgacaaaac  tgatcaccga  cctagccaaa  aaacaaaggg  aggtggtctc  tgatgcaacc       180
gatttcgggt  tggacatcgc  aacaactcta  cagtcaagac  agtcaaacag  tcagttccac       240
```

-continued

```
gtgttgagag aaggaaatgt agataccagg atagcatcgg agagaggatc aacaacacac    300
acaagaaggc ttgccactat tggtaacgtg gagccatgct ggttcagaac agcaccgggt    360
gttagggggg ggatattgat tgaaccctca aacgctgttc tggctctgaa acctctcttc    420
cagggtgcag accccggacc tctttcaagt agtgcccgtt tggatattaa caactattca    480
tcccagacgg cccttggctt catgaacagc attggagcag acatcgaaag taacagggtt    540
tcattttctg agccgttgat tcgcgccttc atcttctcaa ttgatgatca tataagaggt    600
gaatcacccc tctcgtggtt ggggaacaga acgacgcttt tgccgcgccc acttggtaca    660
ttacctagtg gggattactt tccagcatct gtaagatcg ctggatgggt ggcgggagac     720
acacaggcta tgattgtgaa cgctgaagac tttgcaaggg aggcaagggg cgaggagagg    780
ttcaatgacg gttgggggc aacagtatgg aatgtaccag gagtagaagg tgtggcagtt     840
gttcccatta aactcgcaga ccaaggagat ccagcaatca attctatctg gatgctcatg    900
cacatggaaa atccaatccg tacaaggttt gttgaggttg atgaggttga catgttgctg    960
gatgatcctc aggtgggttc agaatggaca aatctttcaa catctgttgt tccgggaccg   1020
tcaaagaagg ttctcttcgt gatcactgac atgaacaaca accagagtgg ggacatactc   1080
ctggacgatt tcaacggtgc tgttgacaac atcgaccaag cagccaacgt cataggagga   1140
gtgccggtcg acatcggagc actaatacct gcctggatgg ggttggatcc tgatcgtcgg   1200
tcagagttgg ggattgctgg agtgaggaga tggacaaggt actatgggaa cacacaggac   1260
tgggaggctt cactagccat cgtgagtgag atgctcgtca cttcccctgg acaggtacag   1320
aggtcaggaa gaacaggtgc tgagaatcac tatgctgatg caggaggagg gattgcccaa   1380
tacccactga atggtattga tgtggtgttg tatgatgggt tgacggctgc agagaagtta   1440
gcattagctg gaagagagtc tgacatcatg actacaccag cttcgggcta caggcagcga   1500
tcaaacaatc caaacacttc gcctccaatg ctcctatact gtcggttttc ctcagaagca   1560
gccgtggctg taagtgctct actctataag cccaggttca caatgaccat cggaaatgag   1620
ttgagacctg ccatcctggc tgataacatc tacaggagag gaaagagaac agcagtcatg   1680
gtggacatca tcgcaggcca gataggtgca gtttctagga tgaccaacac cccagggaac   1740
tcagaacaac cagcagtggc tcaagccatt gttcgtcaac tagcaggctg tgccacacgt   1800
ctacatcagg aaacttgtgc tggtgagcta gtgaacatca ctgtctctgg gtggaataac   1860
caacaaggtc agattgcatg gagaaacctt tacacggatg ccgtgacag aacactgagc    1920 tgcagggtac cacggatgga gtacaactcg ctgggatttg atggaaggat ggaaatcgat   1980
gacctctaca acttcaaaac agagggattc gacgcacttg acattgatgg gcagcagtgg   2040
gatcacatga attggaaaac tccacatcaa aaggaagacg gacaggtcac cgcacgaagg   2100
ctgacttcag cagcaggatg gacaagggct cttgttccac ttgacaacat cggtcttgta   2160
agggctaacg gagcagagtt cgcaccactc ggagtacatg tcctaaaccc aacagttgga   2220
agaggaaagg aagtaagata ttccaactat ggatttgtac cactcgcaag cgagatccga   2280
gagttgccac tggtcacaca ggtaccttca cagaacgatg ccaatcacat cattcaccct   2340
gcagttcgcg gtgaaggcc tctggtgtta ggaaacatgg gaatgttcaa tccaatcttc    2400
atggacagaa ctccgggaca aagagcatcc cagaatccca caaccgacac acagaccgtg   2460
aacaacgcca ccgtcctgga tttc                                          2484
```

<210> SEQ ID NO 2

-continued

```
<211> LENGTH: 1941
<212> TYPE: DNA
<213> ORGANISM: Unknown
<220> FEATURE:
<223> OTHER INFORMATION: Fish totivirus ORF-2 nucleotide sequence

<400> SEQUENCE: 2
atgacaattt taatcaattt tattagagaa aacaaacttg acccatcaaa ggtgttcaaa        60
aatttaacaa acaaggtaaa gttggctggt gagggattca gtagtgactg gaggtattat       120
gtgaactggg aattacttgg tggataccag gatctcgagg aacacgacat gattgaggaa       180
gtaagggctt ttacaacgca ggaagcaaag tcggcagagt tcggagggcc ggttgttaaa       240
gcattggaag aacttcttgc cccttttatca ggagtggtac gttcaaagag aacttttggag      300 gagttcctac tggacagaga tgcatgggcg aagaatacat caggttttgt tacaagtaac       360
atcaagaaag gaaagaacaa gattgaggtt gcagagaaca tggacatcaa agagctactg       420
gagatagttt accttggaga atatcaaaac aggccattta taaaacaaga accaggaaaa       480
gccaggccgg tagttaattc aaacttaccg ccctaccttt tcatgagttg ggttttcgaa       540
caaatcgagc ccattttgag gaaaaacttt tcatcaaaaa ctaccatctt cgattcagca       600
tggacaaaga gtgagttgtg gcatcaaatg acagacgacg tcaggtataa gaaaggaatt       660
ttcgttccgc ttgactattc gagattcgat tcaacaatta gtaaagaact agctgtaaca       720
gcattcaata tgctagttga catactcgtc gacatcccct ctgatctgcg aaggtcagcc       780
aaatacaggt tcaggaatca agtgattctg acgggtgagg aaagttggac gtggaacaat       840
gccgttcttt cgggatggcg ttggactgct ctgattacat cattagtcaa tctcgcaatc       900
ctagaagctg cagaggttac cagaacaggg acgggaatta gagtacaagg ggacgacgtg       960
cgtgttttct ttcaaaagaa aggagatgca gaaattgcaa ttgcgaaaat caactcattc      1020
ggtttcgaaa tcaatccaac aaaagtcttt tgctcgaaaa ggagagatga gtatctaaga      1080
atggtagcaa cggatgaatt acgtggttac ccaattaggt cactcccaaa aatattgttt      1140
gtgggaccaa ctgaaacact taccgacaga tcagaagaca gagtaaatgg aatagtcaac      1200
aaatggacaa cactggtgtc aagaggagga aatgagagta ggtgctggaa gatgcttgtt      1260
accgatattg cgggtttaac ccaatggtca cgtgataaca tcaagaagtg gcttcaaaca      1320
ccttcagcac tgggtggtgc aggactgttc cagaacacaa cgtcacaagg aattagactc      1380
aaaatcaaaa cagagattaa ggaggatttg ggaacttaca agctggcgag tgattacccg      1440
ggagacttgg gaaatttatg ggccagaggt aggaactcaa aatccaagct attgtctgca      1500
caattagaag aaatccacat tccacagcca ttaggagttt ggccaaacgc tttcatcttt      1560
acaaagaaga agaagcccac agttaggttc aaagaagaag cattaggatc cacaaaacgt      1620
gacgccttga ttagggataa ggattgggat gcacttgaag atttggttga gaataagtct      1680
gaggtattgt tttggaagag agtgctcccc agattttct atcgtatgtt gcttgtcgaa       1740
ggaggttttt caactcctat tccaaaaaca ctcgtgaata tgaaatagt tgctacggtc       1800 tcagctttcg tagcgtggta acttttgaa aagatcatga gtataatgg aatattgagt        1860 ggtgaaaagc tccagagact tcaacttggg gcagagtact attcaagatt cttactggac      1920
tcattcaaac gctttggtaa a                                                 1941

<210> SEQ ID NO 3
<211> LENGTH: 270
<212> TYPE: DNA
<213> ORGANISM: Unknown
```

-continued

```
<220> FEATURE:
<223> OTHER INFORMATION: Fish totivirus ORF-X nucleotide sequence

<400> SEQUENCE: 3
atggaaaatg aaaagaacgt aagagtaggt agttgttaca gtgtaagtgc tgtgtttgga      60
tctacaatct gtacagcaca agacaacact gcaggtggag atttggaggc taagcagagc     120
tgggattcac cagttgtgac ggcgatgata gtgatcggag tcgtggcatt cattctgatg     180
gtggtgtgga tgttgagagg agcctgcaag ggctacaccg ttgtgaagag accgcatggg     240
aacgaagagg ctctccaact tcaggacgta                                      270

<210> SEQ ID NO 4
<211> LENGTH: 354
<212> TYPE: DNA
<213> ORGANISM: Unknown
<220> FEATURE:
<223> OTHER INFORMATION: Fish totivirus ORF-Y nucleotide sequence

<400> SEQUENCE: 4
atgtcagtga tgtgggataa cgaatggata aggttgagta gggttagcag gagttctgtt      60
gccgtgaaaa gaaatatata cggtgaacgg gttgaacgct tactactcag ctttggatca     120
gaggcttctg tcttcgaatg gtttggagta gaggaagaag attaccacag gatacgtctg     180
gcattcagag ttattgccca ctgggttatt cactctgaac ttttggaagt aggaggaggg     240
tatacagtct ggagaaatga agatgaccct cgtgaccggg atgcggagtg ggagttctgt     300
tacaccttaa gagttcatgg gagaatggct aactcttcag gcagaagatc agga          354

<210> SEQ ID NO 5
<211> LENGTH: 336
<212> TYPE: DNA
<213> ORGANISM: Unknown
<220> FEATURE:
<223> OTHER INFORMATION: Fish totivirus ORF-Z nucleotide sequence

<400> SEQUENCE: 5
atgatagttt actcttttcaa aaaccacaac cagttgacct ttgcactgga agagcagggt      60
gtggctaatg tcatagttca actagatgac aagtggaagg aggtaacatt tcaacaccat     120
gagaggaaag agttggttca gtttctactc actctcggta aatatgtcga taaagaatta     180
tgtacaacag tactcgactt ggaaattacc gaagaagatg atcttgagta tgaaaaggaa     240
taccaggtga atggtgaaat cttgaccttt tggtctgcag aggttgaagg gaaagaagtc     300
attaatgcaa tgacaatgga gatggaatgt ctcaat                               336

<210> SEQ ID NO 6
<211> LENGTH: 6353
<212> TYPE: DNA
<213> ORGANISM: Unknown
<220> FEATURE:
<223> OTHER INFORMATION: Fish totivirus Genome nucleotide sequence

<400> SEQUENCE: 6
gttagatttg ttttccagtg aggttggttg acggcgcctc accgtaacac tccgtcgggt      60
tcacacgccg ccacgtgtgt cccacccacc actccctccg gtagagtgga ccggtttttcg     120 ctggccagat tgagccctgg tcggtagtcg ggtaacatcg cttaaagggt actgtaggcg     180
tctgaaagca cggattcgac actgtgccgt atggcggtcc tgtccacggt actctactta     240
acttcgcccc cttggaggac cgtacaggtc tgacgtgagg aacttctctg aagtgaccac     300
```

```
aagcgtcgca gtaattgcta gagggaaaga gctgacgggt tgttgagtat tcagtttcta      360
atataccatg gacgcaaaca aagaaacaca aataacagag gagaaagtag gagaggaggt      420
taccttacag gtggaagtaa gggaggaaga tacgggatta ctccaagacc caacgagtaa      480
agaagccctg acaaaactga tcaccgacct agccaaaaaa caaagggagg tggtctctga      540
tgcaaccgat ttcgggttgg acatcgcaac aactctacag tcaagacagt caaacagtca      600
gttccacgtg ttgagagaag gaaatgtaga taccaggata gcatcggaga gaggatcaac      660
aacacacaca agaaggcttg ccactattgg taacgtggag ccatgctggt tcagaacagc      720
accgggtgtt aggggggggga tattgattga accctcaaac gctgttctgg ctctgaaacc      780
tctcttccag ggtgcagacc ccggacctct ttcaagtagt gcccgtttgg atattaacaa      840
ctattcatcc cagacggccc ttggcttcat gaacagcatt ggagcagaca tcgaaagtaa      900
cagggtttca ttttctgagc cgttgattcg cgccttcatc ttctcaattg atgatcatat      960
aagaggtgaa tcacccctct cgtggttggg gaacagaacg acgcttttgc cgcgcccact     1020
tggtacatta cctagtgggg attactttcc agcatctgta agatcagctg gatgggtggc     1080
gggagacaca caggctatga ttgtgaacgc tgaagacttt gcaagggagg caaggggcga     1140
ggagaggttc aatgacggtt gggggggcaac agtatggaat gtaccaggag tagaaggtgt     1200
ggcagttgtt cccattaaac tcgcagacca aggagatcca gcaatcaatt ctatctggat     1260
gctcatgcac atggaaaatc caatccgtac aaggtttgtt gaggttgatg aggttgacat     1320
gttgctggat gatcctcagg tgggttcaga atggacaaat ctttcaacat ctgttgttcc     1380
gggaccgtca aagaaggttc tcttcgtgat cactgacatg aacaacaacc agagtgggga     1440
catactcctg gacgatttca acggtgctgt tgacaacatc gaccaagcag ccaacgtcat     1500
aggaggagtg ccggtcgaca tcggagcact aataacctgcc tggatggggt tggatcctga     1560
tcgtcggtca gagttgggga ttgctggagt gaggagatgg acaaggtact atgggaacac     1620
acaggactgg gaggcttcac tagccatcgt gagtgagatg ctcgtcactt ccctggaca     1680 ggtacagagg tcaggaagaa caggtgctga gaatcactat gctgatgcag gaggagggat     1740
tgcccaatac ccactgaatg gtattgatgt ggtgttgtat gatgggttga cggctgcaga     1800
gaagttagca ttagctggaa gagagtctga catcatgact acaccagctt cgggctacag     1860
gcagcgatca aacaatccaa acacttcgcc tccaatgctc ctatactgtc ggtttttcctc     1920 agaagcagcc gtggctgtaa gtgctctact ctataagccc aggttcacaa tgaccatcgg     1980
aaatgagttg agacctgcca tcctggctga taacatctac aggagaggaa agagaacagc     2040
agtcatggtg gacatcatcg caggccagat aggtgcagtt tctaggatga ccaacacccc     2100
agggaactca gaacaaccag cagtggctca agccattgtt cgtcaactag caggctgtgc     2160
cacacgtcta catcaggaaa cttgtgctgg tgagctagtg aacatcactg tctctgggtg     2220
gaataaccaa caaggtcaga ttgcatggag aaacctttac acggatggcc gtgacagaac     2280
actgagctgc agggtaccac ggatggagta caactcgctg ggatttgatg gaaggatgga     2340
aatcgatgac ctctacaact tcaaaacaga gggattcgac gcacttgaca ttgatgggca     2400
gcagtgggat cacatgaatt ggaaaactcc acatcaaaag gaagacggac aggtcaccgc     2460
acgaaggctg acttcagcag caggatggac aagggctctt gttccacttg acaacatcgg     2520
tcttgtaagg gctaacgag cagagttcgc accactcgga gtacatgtcc taaacccaac     2580
agttggaaga ggaaaggaag taagatattc caactatgga tttgtaccac tcgcaagcga     2640
gatccgagag ttgccactgg tcacacaggt accttcacag aacgatgcca atcacatcat     2700
```

```
tcaccctgca gttcgcggtg gaaggcctct ggtgttagga aacatgggaa tgttcaatcc      2760
aatcttcatg gacagaactc cgggacaaag agcatcccag aatcccacaa ccgacacaca      2820
gaccgtgaac aacgccaccg tcctggattt ctagtaaggg ggagcacgct tcctccttac      2880
cgcgtggacc tacgattcga cccattcttc aaaaattgac aaagaatttc taaaaagaac      2940
aattaggtac taaaatcgac aattgggaag ataacataac atttggaaca acggagaaat      3000
ttaagagtag tggagaacta cctggttggg gaaaaagtgg gtggagaaga ggactgtggt      3060
tggcgttaca agttgttccc cgtgaagtaa aaaatgagat gacaatttta atcaatttta      3120
ttagagaaaa caaacttgac ccatcaaagg tgttcaaaaa tttaacaaac aaggtaaagt      3180
tggctggtga gggattcagt agtgactgga ggtattatgt gaactgggaa ttacttggtg      3240
gataccagga tctcgaggaa cacgacatga ttgaggaagt aagggctttt acaacgcagg      3300
aagcaaagtc ggcagagttc ggagggccgg ttgttaaagc attggaagaa cttcttgccc      3360
ctttatcagg agtggtacgt tcaaagagaa ctttggagga gttcctactg gacagagatg      3420
catgggcgaa gaatacatca ggttttgtta caagtaacat caagaaagga aagaacaaga      3480
ttgaggttgc agagaacatg gacatcaaag agctactgga gatagtttac cttggagaat      3540
atcaaaacag gccatttata aaacaagaac caggaaaagc caggccggta gttaattcaa      3600
acttaccgcc ctacctttc atgagttggg ttttcgaaca aatcgagccc attttgagga      3660 aaaactttc atcaaaaact accatcttcg attcagcatg gacaaagagt gagttgtggc      3720
atcaaatgac agacgacgtc aggtataaga aaggaatttt cgttccgctt gactattcga      3780
gattcgattc aacaattagt aaagaactag ctgtaacagc attcaatatg ctagttgaca      3840
tactcgtcga catcccctct gatctgcgaa ggtcagccaa atacaggttc aggaatcaag      3900
tgattctgac gggtgaggaa agttggacgt ggaacaatgc cgttctttcg ggatggcgtt      3960
ggactgctct gattacatca ttagtcaatc tcgcaatcct agaagctgca gaggttacca      4020
gaacagggac gggaattaga gtacaagggg acgacgtgcg tgttttcttt caaaagaaag      4080
gagatgcaga aattgcaatt gcgaaaatca actcattcgg tttcgaaatc aatccaacaa      4140 aagtctttg ctcgaaaagg agagatgagt atctaagaat ggtagcaacg gatgaattac      4200
gtggttaccc aattaggtca ctcccaaaaa tattgtttgt gggaccaact gaaacactta      4260
ccgacagatc agaagacaga gtaaatggaa tagtcaacaa atggacaaca ctggtgtcaa      4320
gaggaggaaa tgagagtagg tgctggaaga tgcttgttac cgatattgcg ggtttaaccc      4380
aatggtcacg tgataacatc aagaagtggc ttcaaacacc ttcagcactg ggtggtgcag      4440
gactgttcca gaacacaacg tcacaaggaa ttagactcaa aatcaaaaca gagattaagg      4500
aggatttggg aacttacaag ctggcgagtg attacccggg agacttggga aatttatggg      4560
ccagaggtag gaactcaaaa tccaagctat tgtctgcaca attagaagaa atccacattc      4620
cacagccatt aggagtttgg ccaaacgctt tcatctttac aaagaagaag aagcccacag      4680
ttaggttcaa agaagaagca ttaggatcca caaaacgtga cgccttgatt agggataagg      4740
attgggatgc acttgaagat ttggttgaga ataagtctga ggtattgttt tggaagagag      4800
tgctccccag attttctat cgtatgttgc ttgtcgaagg aggttttca actcctattc       4860 caaaaacact cgtgaataat gaaatagttg ctacggtctc agctttcgta gcgtggtata       4920
cttttgaaaa gatcatgaag tataatggaa tattgagtgg tgaaaagctc cagagacttc      4980
aacttggggc agagtactat tcaagattct tactggactc attcaaacgc tttggtaaat      5040
```

-continued

```
aatgcaatgt acgggagtcg gtcaggaccg tacagtatca acacgaatgt agatttgttc   5100
tacgacggtg ggcaaatagt tgctaaacgg taagtccatc cgaggcggct tacctgtagt   5160
taccctggag acaaagggaa taaacacgaa gtgtgaccct cctagtaagg cccaggaacg   5220
tgccgcgtaa ctatgggtat cggcaataca tgacaaaatg gaaatgaaa agaacgtaag    5280 agtaggtagt tgttacagtg taagtgctgt gtttggatct acaatctgta cagcacaaga   5340
caacactgca ggtggagatt tggaggctaa gcagagctgg gattcaccag ttgtgacggc   5400
gatgatagtg atcggagtcg tggcattcat tctgatggtg gtgtggatgt tgagaggagc   5460
ctgcaagggc tacaccgttg tgaagagacc gcatgggaac gaagaggctc tccaacttca   5520
ggacgtataa tgtcagtgat gtgggataac gaatggataa ggttgagtag ggttagcagg   5580
agttctgttg ccgtgaaaag aaatatatac ggtgaacggg ttgaacgctt actactcagc   5640
tttggatcag aggcttctgt cttcgaatgg tttggagtag aggaagaaga ttaccacagg   5700
atacgtctgg cattcagagt tattgcccac tgggttattc actctgaact tttggaagta   5760
ggaggagggt atacagtctg gagaaatgaa gatgaccctc gtgaccggga tgcggagtgg   5820
gagttctgtt acaccttaag agttcatggg agaatggcta actcttcagg cagaagatca   5880
ggatgatagt ttactctttc aaaaaccaca accagttgac ctttgcactg gaagagcagg   5940
gtgtggctaa tgtcatagtt caactagatg acaagtggaa ggaggtaaca tttcaacacc   6000
atgagaggaa agagttggtt cagtttctac tcactctcgg taaatatgtc gataaagaat   6060
tatgtacaac agtactcgac ttggaaatta ccgaagaaga tgatcttgag tatgaaaagg   6120
aataccaggt gaatggtgaa atcttgacct tttggtctgc agaggttgaa gggaaagaag   6180
tcattaatgc aatgacaatg gagatggaat gtctcaatta attctctctt atagagaggc   6240
acagcatcac acaacacaca ctcacacaca ccaacgcaca cactaggctg gcgggcctat   6300
aggagtaccc ctgactccga atataaatct aatgggggcc tgtagttaag cac          6353
```

<210> SEQ ID NO 7
<211> LENGTH: 828
<212> TYPE: PRT
<213> ORGANISM: Unknown
<220> FEATURE:
<223> OTHER INFORMATION: Fish totivirus ORF-1 amino acid sequence

<400> SEQUENCE: 7

```
Met Asp Ala Asn Lys Glu Thr Gln Ile Thr Glu Glu Lys Val Gly Glu
1               5                   10                  15

Glu Val Thr Leu Gln Val Glu Val Arg Glu Glu Asp Thr Gly Leu Leu
            20                  25                  30

Gln Asp Pro Thr Ser Lys Glu Ala Leu Thr Lys Leu Ile Thr Asp Leu
        35                  40                  45

Ala Lys Lys Gln Arg Glu Val Val Ser Asp Ala Thr Asp Phe Gly Leu
    50                  55                  60

Asp Ile Ala Thr Thr Leu Gln Ser Arg Gln Ser Asn Ser Gln Phe His
65                  70                  75                  80

Val Leu Arg Glu Gly Asn Val Asp Thr Arg Ile Ala Ser Glu Arg Gly
                85                  90                  95

Ser Thr Thr His Thr Arg Arg Leu Ala Thr Ile Gly Asn Val Glu Pro
            100                 105                 110

Cys Trp Phe Arg Thr Ala Pro Gly Val Arg Gly Gly Ile Leu Ile Glu
        115                 120                 125

Pro Ser Asn Ala Val Leu Ala Leu Lys Pro Leu Phe Gln Gly Ala Asp
```

-continued

```
             130               135               140
Pro Gly Pro Leu Ser Ser Ser Ala Arg Leu Asp Ile Asn Asn Tyr Ser
145                 150               155               160

Ser Gln Thr Ala Leu Gly Phe Met Asn Ser Ile Gly Ala Asp Ile Glu
                165               170               175

Ser Asn Arg Val Ser Phe Ser Glu Pro Leu Ile Arg Ala Phe Ile Phe
                180               185               190

Ser Ile Asp Asp His Ile Arg Gly Glu Ser Pro Leu Ser Trp Leu Gly
            195               200               205

Asn Arg Thr Thr Leu Leu Pro Arg Pro Leu Gly Thr Leu Pro Ser Gly
        210               215               220

Asp Tyr Phe Pro Ala Ser Val Arg Ser Ala Gly Trp Val Ala Gly Asp
225               230               235               240

Thr Gln Ala Met Ile Val Asn Ala Glu Asp Phe Ala Arg Glu Ala Arg
                245               250               255

Gly Glu Glu Arg Phe Asn Asp Gly Trp Gly Ala Thr Val Trp Asn Val
                260               265               270

Pro Gly Val Glu Gly Val Ala Val Val Pro Ile Lys Leu Ala Asp Gln
            275               280               285

Gly Asp Pro Ala Ile Asn Ser Ile Trp Met Leu Met His Met Glu Asn
        290               295               300

Pro Ile Arg Thr Arg Phe Val Glu Val Asp Glu Val Asp Met Leu Leu
305               310               315               320

Asp Asp Pro Gln Val Gly Ser Glu Trp Thr Asn Leu Ser Thr Ser Val
                325               330               335

Val Pro Gly Pro Ser Lys Lys Val Leu Phe Val Ile Thr Asp Met Asn
                340               345               350

Asn Asn Gln Ser Gly Asp Ile Leu Leu Asp Asp Phe Asn Gly Ala Val
            355               360               365

Asp Asn Ile Asp Gln Ala Ala Asn Val Ile Gly Gly Val Pro Val Asp
        370               375               380

Ile Gly Ala Leu Ile Pro Ala Trp Met Gly Leu Asp Pro Asp Arg Arg
385               390               395               400

Ser Glu Leu Gly Ile Ala Gly Val Arg Arg Trp Thr Arg Tyr Tyr Gly
                405               410               415

Asn Thr Gln Asp Trp Glu Ala Ser Leu Ala Ile Val Ser Glu Met Leu
            420               425               430

Val Thr Phe Pro Gly Gln Val Gln Arg Ser Gly Arg Thr Gly Ala Glu
            435               440               445

Asn His Tyr Ala Asp Ala Gly Gly Gly Ile Ala Gln Tyr Pro Leu Asn
        450               455               460

Gly Ile Asp Val Val Leu Tyr Asp Gly Leu Thr Ala Ala Glu Lys Leu
465               470               475               480

Ala Leu Ala Gly Arg Glu Ser Asp Ile Met Thr Thr Pro Ala Ser Gly
                485               490               495

Tyr Arg Gln Arg Ser Asn Asn Pro Asn Thr Ser Pro Pro Met Leu Leu
            500               505               510

Tyr Cys Arg Phe Ser Ser Glu Ala Ala Val Ala Val Ser Ala Leu Leu
            515               520               525

Tyr Lys Pro Arg Phe Thr Met Thr Ile Gly Asn Glu Leu Arg Pro Ala
        530               535               540

Ile Leu Ala Asp Asn Ile Tyr Arg Arg Gly Lys Arg Thr Ala Val Met
545               550               555               560
```

-continued

```
Val Asp Ile Ile Ala Gly Gln Ile Gly Ala Val Ser Arg Met Thr Asn
            565             570             575

Thr Pro Gly Asn Ser Glu Gln Pro Ala Val Ala Gln Ala Ile Val Arg
            580             585             590

Gln Leu Ala Gly Cys Ala Thr Arg Leu His Gln Glu Thr Cys Ala Gly
            595             600             605

Glu Leu Val Asn Ile Thr Val Ser Gly Trp Asn Asn Gln Gln Gly Gln
            610             615             620

Ile Ala Trp Arg Asn Leu Tyr Thr Asp Gly Arg Asp Arg Thr Leu Ser
625             630             635             640

Cys Arg Val Pro Arg Met Glu Tyr Asn Ser Leu Gly Phe Asp Gly Arg
            645             650             655

Met Glu Ile Asp Asp Leu Tyr Asn Phe Lys Thr Glu Gly Phe Asp Ala
            660             665             670

Leu Asp Ile Asp Gly Gln Gln Trp Asp His Met Asn Trp Lys Thr Pro
            675             680             685

His Gln Lys Glu Asp Gly Gln Val Thr Ala Arg Arg Leu Thr Ser Ala
            690             695             700

Ala Gly Trp Thr Arg Ala Leu Val Pro Leu Asp Asn Ile Gly Leu Val
705             710             715             720

Arg Ala Asn Gly Ala Glu Phe Ala Pro Leu Gly Val His Val Leu Asn
            725             730             735

Pro Thr Val Gly Arg Gly Lys Glu Val Arg Tyr Ser Asn Tyr Gly Phe
            740             745             750

Val Pro Leu Ala Ser Glu Ile Arg Glu Leu Pro Leu Val Thr Gln Val
            755             760             765

Pro Ser Gln Asn Asp Ala Asn His Ile Ile His Pro Ala Val Arg Gly
            770             775             780

Gly Arg Pro Leu Val Leu Gly Asn Met Gly Met Phe Asn Pro Ile Phe
785             790             795             800

Met Asp Arg Thr Pro Gly Gln Arg Ala Ser Gln Asn Pro Thr Thr Asp
            805             810             815

Thr Gln Thr Val Asn Asn Ala Thr Val Leu Asp Phe
            820             825
```

<210> SEQ ID NO 8
<211> LENGTH: 647
<212> TYPE: PRT
<213> ORGANISM: Unknown
<220> FEATURE:
<223> OTHER INFORMATION: Fish totivirus ORF-2 amino acid sequence

<400> SEQUENCE: 8

```
Met Thr Ile Leu Ile Asn Phe Ile Arg Glu Asn Lys Leu Asp Pro Ser
1               5               10              15

Lys Val Phe Lys Asn Leu Thr Asn Lys Val Lys Leu Ala Gly Glu Gly
            20              25              30

Phe Ser Ser Asp Trp Arg Tyr Tyr Val Asn Trp Glu Leu Leu Gly Gly
            35              40              45

Tyr Gln Asp Leu Glu Glu His Asp Met Ile Glu Glu Val Arg Ala Phe
            50              55              60

Thr Thr Gln Glu Ala Lys Ser Ala Glu Phe Gly Gly Pro Val Val Lys
65              70              75              80

Ala Leu Glu Glu Leu Leu Ala Pro Leu Ser Gly Val Val Arg Ser Lys
            85              90              95
```

-continued

```
Arg Thr Leu Glu Glu Phe Leu Leu Asp Arg Asp Ala Trp Ala Lys Asn
            100                 105                 110

Thr Ser Gly Phe Val Thr Ser Asn Ile Lys Lys Gly Lys Asn Lys Ile
            115                 120                 125

Glu Val Ala Glu Asn Met Asp Ile Lys Glu Leu Leu Glu Ile Val Tyr
            130                 135                 140

Leu Gly Glu Tyr Gln Asn Arg Pro Phe Ile Lys Gln Glu Pro Gly Lys
145                 150                 155                 160

Ala Arg Pro Val Val Asn Ser Asn Leu Pro Pro Tyr Leu Phe Met Ser
                165                 170                 175

Trp Val Phe Glu Gln Ile Glu Pro Ile Leu Arg Lys Asn Phe Ser Ser
            180                 185                 190

Lys Thr Thr Ile Phe Asp Ser Ala Trp Thr Lys Ser Glu Leu Trp His
            195                 200                 205

Gln Met Thr Asp Asp Val Arg Tyr Lys Lys Gly Ile Phe Val Pro Leu
            210                 215                 220

Asp Tyr Ser Arg Phe Asp Ser Thr Ile Ser Lys Glu Leu Ala Val Thr
225                 230                 235                 240

Ala Phe Asn Met Leu Val Asp Ile Leu Val Asp Ile Pro Ser Asp Leu
                245                 250                 255

Arg Arg Ser Ala Lys Tyr Arg Phe Arg Asn Gln Val Ile Leu Thr Gly
                260                 265                 270

Glu Glu Ser Trp Thr Trp Asn Asn Ala Val Leu Ser Gly Trp Arg Trp
            275                 280                 285

Thr Ala Leu Ile Thr Ser Leu Val Asn Leu Ala Ile Leu Glu Ala Ala
            290                 295                 300

Glu Val Thr Arg Thr Gly Thr Gly Ile Arg Val Gln Gly Asp Asp Val
305                 310                 315                 320

Arg Val Phe Phe Gln Lys Lys Gly Asp Ala Glu Ile Ala Ile Ala Lys
                325                 330                 335

Ile Asn Ser Phe Gly Phe Glu Ile Asn Pro Thr Lys Val Phe Cys Ser
                340                 345                 350

Lys Arg Arg Asp Glu Tyr Leu Arg Met Val Ala Thr Asp Glu Leu Arg
            355                 360                 365

Gly Tyr Pro Ile Arg Ser Leu Pro Lys Ile Leu Phe Val Gly Pro Thr
            370                 375                 380

Glu Thr Leu Thr Asp Arg Ser Glu Asp Arg Val Asn Gly Ile Val Asn
385                 390                 395                 400

Lys Trp Thr Thr Leu Val Ser Arg Gly Gly Asn Glu Ser Arg Cys Trp
                405                 410                 415

Lys Met Leu Val Thr Asp Ile Ala Gly Leu Thr Gln Trp Ser Arg Asp
                420                 425                 430

Asn Ile Lys Lys Trp Leu Gln Thr Pro Ser Ala Leu Gly Gly Ala Gly
            435                 440                 445

Leu Phe Gln Asn Thr Thr Ser Gln Gly Ile Arg Leu Lys Ile Lys Thr
            450                 455                 460

Glu Ile Lys Glu Asp Leu Gly Thr Tyr Lys Leu Ala Ser Asp Tyr Pro
465                 470                 475                 480

Gly Asp Leu Gly Asn Leu Trp Ala Arg Gly Arg Asn Ser Lys Ser Lys
                485                 490                 495

Leu Leu Ser Ala Gln Leu Glu Glu Ile His Ile Pro Gln Pro Leu Gly
            500                 505                 510
```

```
Val Trp Pro Asn Ala Phe Ile Phe Thr Lys Lys Lys Pro Thr Val
        515             520             525

Arg Phe Lys Glu Glu Ala Leu Gly Ser Thr Lys Arg Asp Ala Leu Ile
        530             535             540

Arg Asp Lys Asp Trp Asp Ala Leu Glu Asp Leu Val Glu Asn Lys Ser
545             550             555             560

Glu Val Leu Phe Trp Lys Arg Val Leu Pro Arg Phe Phe Tyr Arg Met
                565             570             575

Leu Leu Val Glu Gly Gly Phe Ser Thr Pro Ile Pro Lys Thr Leu Val
                580             585             590

Asn Asn Glu Ile Val Ala Thr Val Ser Ala Phe Val Ala Trp Tyr Thr
        595             600             605

Phe Glu Lys Ile Met Lys Tyr Asn Gly Ile Leu Ser Gly Glu Lys Leu
        610             615             620

Gln Arg Leu Gln Leu Gly Ala Glu Tyr Tyr Ser Arg Phe Leu Leu Asp
625             630             635             640

Ser Phe Lys Arg Phe Gly Lys
                645

<210> SEQ ID NO 9
<211> LENGTH: 90
<212> TYPE: PRT
<213> ORGANISM: Unknown
<220> FEATURE:
<223> OTHER INFORMATION: Fish totivirus ORF-X amino acid sequence

<400> SEQUENCE: 9

Met Glu Asn Glu Lys Asn Val Arg Val Gly Ser Cys Tyr Ser Val Ser
1               5               10              15

Ala Val Phe Gly Ser Thr Ile Cys Thr Ala Gln Asp Asn Thr Ala Gly
            20              25              30

Gly Asp Leu Glu Ala Lys Gln Ser Trp Asp Ser Pro Val Val Thr Ala
        35              40              45

Met Ile Val Ile Gly Val Val Ala Phe Ile Leu Met Val Val Trp Met
    50              55              60

Leu Arg Gly Ala Cys Lys Gly Tyr Thr Val Val Lys Arg Pro His Gly
65              70              75              80

Asn Glu Glu Ala Leu Gln Leu Gln Asp Val
                85              90

<210> SEQ ID NO 10
<211> LENGTH: 118
<212> TYPE: PRT
<213> ORGANISM: Unknown
<220> FEATURE:
<223> OTHER INFORMATION: Fish totivirus ORF-Y amino acid sequence

<400> SEQUENCE: 10

Met Ser Val Met Trp Asp Asn Glu Trp Ile Arg Leu Ser Arg Val Ser
1               5               10              15

Arg Ser Ser Val Ala Val Lys Arg Asn Ile Tyr Gly Glu Arg Val Glu
            20              25              30

Arg Leu Leu Leu Ser Phe Gly Ser Glu Ala Ser Val Phe Glu Trp Phe
        35              40              45

Gly Val Glu Glu Glu Asp Tyr His Arg Ile Arg Leu Ala Phe Arg Val
    50              55              60

Ile Ala His Trp Val Ile His Ser Glu Leu Leu Glu Val Gly Gly Gly
65              70              75              80
```

Tyr Thr Val Trp Arg Asn Glu Asp Asp Pro Arg Asp Arg Asp Ala Glu
                85                  90                  95

Trp Glu Phe Cys Tyr Thr Leu Arg Val His Gly Arg Met Ala Asn Ser
        100                 105                 110

Ser Gly Arg Arg Ser Gly
        115

<210> SEQ ID NO 11
<211> LENGTH: 112
<212> TYPE: PRT
<213> ORGANISM: Unknown
<220> FEATURE:
<223> OTHER INFORMATION: Fish totivirus ORF-Z amino acid sequence

<400> SEQUENCE: 11

Met Ile Val Tyr Ser Phe Lys Asn His Asn Gln Leu Thr Phe Ala Leu
1               5                   10                  15

Glu Glu Gln Gly Val Ala Asn Val Ile Val Gln Leu Asp Asp Lys Trp
        20                  25                  30

Lys Glu Val Thr Phe Gln His His Glu Arg Lys Glu Leu Val Gln Phe
        35                  40                  45

Leu Leu Thr Leu Gly Lys Tyr Val Asp Lys Glu Leu Cys Thr Thr Val
    50                  55                  60

Leu Asp Leu Glu Ile Thr Glu Glu Asp Asp Leu Glu Tyr Glu Lys Glu
65                  70                  75                  80

Tyr Gln Val Asn Gly Glu Ile Leu Thr Phe Trp Ser Ala Glu Val Glu
                85                  90                  95

Gly Lys Glu Val Ile Asn Ala Met Thr Met Glu Met Glu Cys Leu Asn
        100                 105                 110

<210> SEQ ID NO 12
<211> LENGTH: 21
<212> TYPE: DNA
<213> ORGANISM: Artificial Sequence
<220> FEATURE:
<223> OTHER INFORMATION: CLP01 Forward primer

<400> SEQUENCE: 12
ctgtggctgt aagtgctcta c                                                 21

<210> SEQ ID NO 13
<211> LENGTH: 25
<212> TYPE: DNA
<213> ORGANISM: Artificial Sequence
<220> FEATURE:
<223> OTHER INFORMATION: CLP01 Taqman Probe

<400> SEQUENCE: 13
tttccgatgg tcattgtgaa cctgg                                             25

<210> SEQ ID NO 14
<211> LENGTH: 21
<212> TYPE: DNA
<213> ORGANISM: Artificial Sequence
<220> FEATURE:
<223> OTHER INFORMATION: CLP01 Reverse primer

<400> SEQUENCE: 14
gctgttctct ttcctctcct g                                                 21

<210> SEQ ID NO 15

```
<211> LENGTH: 21
<212> TYPE: DNA
<213> ORGANISM: Artificial Sequence
<220> FEATURE:
<223> OTHER INFORMATION: CLP02 Forward primer

<400> SEQUENCE: 15
tcagccaaat acaggttcag g                                                      21

<210> SEQ ID NO 16
<211> LENGTH: 24
<212> TYPE: DNA
<213> ORGANISM: Artificial Sequence
<220> FEATURE:
<223> OTHER INFORMATION: CLP02 Taqman Probe

<400> SEQUENCE: 16
ccaactttcc tcacccgtca gaat                                                   24

<210> SEQ ID NO 17
<211> LENGTH: 21
<212> TYPE: DNA
<213> ORGANISM: Artificial Sequence
<220> FEATURE:
<223> OTHER INFORMATION: CLP02 Reverse primer

<400> SEQUENCE: 17
tgtaatcaga gcagtccaac g                                                      21

<210> SEQ ID NO 18
<211> LENGTH: 22
<212> TYPE: DNA
<213> ORGANISM: Artificial Sequence
<220> FEATURE:
<223> OTHER INFORMATION: CLP03 Forward primer

<400> SEQUENCE: 18
agtgatgtgg gataacgaat gg                                                     22

<210> SEQ ID NO 19
<211> LENGTH: 24
<212> TYPE: DNA
<213> ORGANISM: Artificial Sequence
<220> FEATURE:
<223> OTHER INFORMATION: CLP03 Taqman Probe

<400> SEQUENCE: 19
aggttgagta gggttagcag gagt                                                   24

<210> SEQ ID NO 20
<211> LENGTH: 22
<212> TYPE: DNA
<213> ORGANISM: Artificial Sequence
<220> FEATURE:
<223> OTHER INFORMATION: CLP03 Reverse primer

<400> SEQUENCE: 20
cctctgatcc aaagctgagt ag                                                     22

<210> SEQ ID NO 21
<211> LENGTH: 21
<212> TYPE: DNA
<213> ORGANISM: Artificial Sequence
<220> FEATURE:
<223> OTHER INFORMATION: PCL_F1

<400> SEQUENCE: 21
```

-continued atggacgcaa acaaagaaac a                                                    21

<210> SEQ ID NO 22
<211> LENGTH: 20
<212> TYPE: DNA
<213> ORGANISM: Artificial Sequence
<220> FEATURE:
<223> OTHER INFORMATION: PCL_R1

<400> SEQUENCE: 22
ccaatgctgt tcatgaaacc                                                      20

<210> SEQ ID NO 23
<211> LENGTH: 21
<212> TYPE: DNA
<213> ORGANISM: Artificial Sequence
<220> FEATURE:
<223> OTHER INFORMATION: PCL_F2

<400> SEQUENCE: 23
ccggacctct ttcaagtagt g                                                    21

<210> SEQ ID NO 24
<211> LENGTH: 20
<212> TYPE: DNA
<213> ORGANISM: Artificial Sequence
<220> FEATURE:
<223> OTHER INFORMATION: PCL_R2

<400> SEQUENCE: 24
gcatctcact cacgatggct                                                      20

<210> SEQ ID NO 25
<211> LENGTH: 20
<212> TYPE: DNA
<213> ORGANISM: Artificial Sequence
<220> FEATURE:
<223> OTHER INFORMATION: PCL_F3

<400> SEQUENCE: 25
tgggaacaca caggactggg                                                      20

<210> SEQ ID NO 26
<211> LENGTH: 20
<212> TYPE: DNA
<213> ORGANISM: Artificial Sequence
<220> FEATURE:
<223> OTHER INFORMATION: PCL_R3

<400> SEQUENCE: 26
ctccatgcaa tctgaccttg                                                      20

<210> SEQ ID NO 27
<211> LENGTH: 22
<212> TYPE: DNA
<213> ORGANISM: Artificial Sequence
<220> FEATURE:
<223> OTHER INFORMATION: PCL_F4

<400> SEQUENCE: 27
acttgtgctg gtgagctagt ga                                                   22

<210> SEQ ID NO 28
<211> LENGTH: 17
<212> TYPE: DNA

```
<213> ORGANISM: Artificial Sequence
<220> FEATURE:
<223> OTHER INFORMATION: PCL_R4

<400> SEQUENCE: 28
atccaggacg gtggcgt                                                    17

<210> SEQ ID NO 29
<211> LENGTH: 25
<212> TYPE: DNA
<213> ORGANISM: Artificial Sequence
<220> FEATURE:
<223> OTHER INFORMATION: PCL_F5

<400> SEQUENCE: 29
ttagagaaaa caaacttgac ccatc                                          25

<210> SEQ ID NO 30
<211> LENGTH: 25
<212> TYPE: DNA
<213> ORGANISM: Artificial Sequence
<220> FEATURE:
<223> OTHER INFORMATION: PCL_R5

<400> SEQUENCE: 30
cgacgagtat gtcaactagc atatt                                          25

<210> SEQ ID NO 31
<211> LENGTH: 21
<212> TYPE: DNA
<213> ORGANISM: Artificial Sequence
<220> FEATURE:
<223> OTHER INFORMATION: PCL_F6

<400> SEQUENCE: 31
caaatgacag acgacgtcag g                                              21

<210> SEQ ID NO 32
<211> LENGTH: 20
<212> TYPE: DNA
<213> ORGANISM: Artificial Sequence
<220> FEATURE:
<223> OTHER INFORMATION: PCL_R6

<400> SEQUENCE: 32
ccagtgctga aggtgtttga                                                20

<210> SEQ ID NO 33
<211> LENGTH: 22
<212> TYPE: DNA
<213> ORGANISM: Artificial Sequence
<220> FEATURE:
<223> OTHER INFORMATION: PCL_F7

<400> SEQUENCE: 33
ccgatattgc gggtttaacc ca                                             22

<210> SEQ ID NO 34
<211> LENGTH: 20
<212> TYPE: DNA
<213> ORGANISM: Artificial Sequence
<220> FEATURE:
<223> OTHER INFORMATION: PCL_R7

<400> SEQUENCE: 34
cgctacgaaa gctgagaccg                                                20
```

```
<210> SEQ ID NO 35
<211> LENGTH: 25
<212> TYPE: DNA
<213> ORGANISM: Artificial Sequence
<220> FEATURE:
<223> OTHER INFORMATION: PCL_F8

<400> SEQUENCE: 35
gttgttacag tgtaagtgct gtgtt                                         25

<210> SEQ ID NO 36
<211> LENGTH: 25
<212> TYPE: DNA
<213> ORGANISM: Artificial Sequence
<220> FEATURE:
<223> OTHER INFORMATION: PCL_R8

<400> SEQUENCE: 36
ttaccgagag tgagtagaaa ctgaa                                         25

<210> SEQ ID NO 37
<211> LENGTH: 17
<212> TYPE: DNA
<213> ORGANISM: Artificial Sequence
<220> FEATURE:
<223> OTHER INFORMATION: PCL_F9

<400> SEQUENCE: 37
acgccaccgt cctggat                                                  17

<210> SEQ ID NO 38
<211> LENGTH: 21
<212> TYPE: DNA
<213> ORGANISM: Artificial Sequence
<220> FEATURE:
<223> OTHER INFORMATION: PCL_R9

<400> SEQUENCE: 38
cctgacgtcg tctgtcattt g                                             21

<210> SEQ ID NO 39
<211> LENGTH: 20
<212> TYPE: DNA
<213> ORGANISM: Artificial Sequence
<220> FEATURE:
<223> OTHER INFORMATION: PCL_F10

<400> SEQUENCE: 39
cggtctcagc tttcgtagcg                                               20

<210> SEQ ID NO 40
<211> LENGTH: 25
<212> TYPE: DNA
<213> ORGANISM: Artificial Sequence
<220> FEATURE:
<223> OTHER INFORMATION: PCL_R10

<400> SEQUENCE: 40
aacacagcac ttacactgta acaac                                         25

<210> SEQ ID NO 41
<211> LENGTH: 25
<212> TYPE: DNA
<213> ORGANISM: Artificial Sequence
<220> FEATURE:
```

-continued

```
<223> OTHER INFORMATION: primer

<400> SEQUENCE: 41
cctacactta cagccacaga gtgcc                                          25

<210> SEQ ID NO 42
<211> LENGTH: 37
<212> TYPE: DNA
<213> ORGANISM: Artificial Sequence
<220> FEATURE:
<223> OTHER INFORMATION: primer

<400> SEQUENCE: 42
tggtggcggc gctagctgtc aggagaggaa agagaag                            37

<210> SEQ ID NO 43
<211> LENGTH: 122
<212> TYPE: DNA
<213> ORGANISM: Artificial Sequence
<220> FEATURE:
<223> OTHER INFORMATION: primer

<400> SEQUENCE: 43
actcaacata aagttatact catggctaaa atttattaca ctacaggaac agcaggaaaa    60
cgatgggtgt aggtgaaggc tagagaagcc aaatacaggt tttcttatct tccttttgtg   120
gg                                                                  122

<210> SEQ ID NO 44
<211> LENGTH: 25
<212> TYPE: DNA
<213> ORGANISM: Artificial Sequence
<220> FEATURE:
<223> OTHER INFORMATION: primer

<400> SEQUENCE: 44
tgcaggtatt tcctcacccg tcagc                                          25

<210> SEQ ID NO 45
<211> LENGTH: 54
<212> TYPE: DNA
<213> ORGANISM: Artificial Sequence
<220> FEATURE:
<223> OTHER INFORMATION: primer

<400> SEQUENCE: 45
agtacatcat acaatacatg atcaactgct ctgattacat tattaattga aatt          54

<210> SEQ ID NO 46
<211> LENGTH: 23
<212> TYPE: DNA
<213> ORGANISM: Artificial Sequence
<220> FEATURE:
<223> OTHER INFORMATION: primer

<400> SEQUENCE: 46
caggttcaca atgaccacct cat                                            23

<210> SEQ ID NO 47
<211> LENGTH: 25
<212> TYPE: DNA
<213> ORGANISM: Artificial Sequence
<220> FEATURE:
<223> OTHER INFORMATION: primer

<400> SEQUENCE: 47
```

-continued

```
cgatgtggga taacgaaccg ggtaa                                          25

<210> SEQ ID NO 48
<211> LENGTH: 121
<212> TYPE: DNA
<213> ORGANISM: Artificial Sequence
<220> FEATURE:
<223> OTHER INFORMATION: primer

<400> SEQUENCE: 48
ttacagggtt cctgcctaaa tgaatcatca tccaaggatt tacaaaaaat tatagccttg      60
kcaccccaac cattatagct atcataaccc tactcaacct gtactcttac atacacctca     120
t                                                                     121

<210> SEQ ID NO 49
<211> LENGTH: 97
<212> TYPE: DNA
<213> ORGANISM: Artificial Sequence
<220> FEATURE:
<223> OTHER INFORMATION: primer

<400> SEQUENCE: 49
tatcacatcc acttgatcca aagctgagtt gaggttctga atacctttgt taattttctg      60
tctcaatgac ctaatattgt cagtggagtg ttaaatc                               97
```

FISH TOTIVIRUS

CROSS REFERENCE TO RELATED APPLICATIONS

This Application is the National Stage of International Application No. PCT/EP2020/052683, filed on Feb. 4, 2020, which application claims the benefit of European Application No. 19155628.1, filed on Feb. 5, 2019.

FIELD OF THE INVENTION

The invention inter alia relates to a novel fish virus, indicated to be a Totivirus, which causes mortality in fish, and to methods of detecting said virus in fish and protecting fish from infection by said virus, and related (re) agents and uses.

BACKGROUND OF THE INVENTION

Fish are a major source of food and fish farming has become an important industry, particularly as rates of wild fish capture are flat or declining due to overfishing and loss of habitat. Examples of fish that are farmed include Atlantic salmon (*Salmo salar*) and lumpsucker (*Cyclopterus lumpus*).

However, infectious diseases in aquaculture threaten fish production and may also impact wild fish populations. For example, heart and skeletal muscle inflammation (HSMI) is known to be a frequently fatal disease of farmed Atlantic salmon. Affected fish often show reduced appetite prior to abnormal swimming behaviour and in some cases, sudden death. Usually, no external lesions are recognized. At autopsy, the heart often appears pale and somewhat loose. In some cases, the pericardial sac is filled with blood. Histological examinations indicate that most fish in affected net cages show severe lesions, although they seemingly appear to be healthy. First recognized in Norway in 1999 (Kongtorp et al., J Fish Dis 27, 2004), HSMI was subsequently implicated in several outbreaks in other farms in Norway and the United Kingdom. It is believed that piscine reovirus (PRV), a fish reovirus belongs to the family Reoviridae, subfamily Spinareovirinae, is the likely causative agent of HSMI (Kibenge et al., Virol J. 10, 2013). Since 1999 there has been an increasing number of outbreaks and the disease is considered to have a detrimental economic impact on the salmon farming industry.

Cardiomyopathy syndrome (CMS) is a severe cardiac disease affecting primarily large Atlantic salmon in the second year in seawater close to harvest. Affected fish may suddenly die without showing outward signs of disease, or may show symptoms such as abnormal swimming behaviour and anorexia. The disease was first recognized in farmed Atlantic salmon in Norway in 1985 and subsequently in farmed salmon in the Faroe Islands, the United Kingdom and Ireland. CMS has also been described in wild Atlantic salmon in Norway. In 2010, a double-stranded RNA virus of the Totiviridae family, named piscine myocarditis virus (PMCV), was described as the causative agent of CMS (Haugland et al, J. Virol, 85, 2011). PMCV is considered one of the largest problems in Atlantic salmon production, leading to major financial losses for salmon producing companies.

Disease challenges in the production of lumpfish (*Cyclopterus lumpus*) have to a certain degree been dominated by bacterial infections. Among these, *Aeromonas salmonicida* subsp. (atypical furunculosis), *Pasteurella* sp., *Vibrio* anguillarum and *Tenacibaculum* sp. have been the most significant species. The application of targeted vaccination programs, systematic monitoring of disease and improvements in production has led to a gradual decrease of the number of cases of atypical furuncolosis, vibriosis and pasteurellosis. However, several species of viruses have been detected in wild lumpfish, including viral hemorrhagic septicemia (VHSV) (Guðmundsdóttir et al, J. Fish Dis, 42, 2019), viral nervous necrosis (VNN) and a novel ranavirus. Recently, a virus affecting farmed lumpfish has been identified: lumpfish flavivirus (LFV/CLuV) (Skoge et al, Arch Virol, 163, 2018). LFV/CLuV shows low but distinct similarity to the unassigned Tamana bat virus (TABV). LFV/CLuV was found to be present in all kinds of lumpfish tissues of affected fish, but pathology was primarily observed in the liver and kidneys. The virus is associated with serious disease in lumpfish. After LFV/CLuV was characterized, mapping the distribution of the virus and its association with disease has shown that it is widespread, with a relatively high associated prevalence.

Certain fish farms currently experience high mortality—for example up to 80% in some lumpsucker populations—despite real-time RT-PCR and histology failing to find any known pathogens in the fish.

Thus, there is an ongoing need to identify further pathogens which infect and which kill fish, particularly farmed lumpsucker fish. Further, there is an ongoing need for methods of monitoring the production of farmed fish for the presence of infection by pathogens, to avoid outbreaks of infection and potentially to treat infected fish.

SUMMARY OF THE INVENTION

The present invention has surprisingly found a novel virus in lumpsucker fish, herein termed *Cyclopterus lumpus* Totivirus (CLuTV). The length and organization of the genome, together with sequence analyses, indicate that CLuTV is a Totivirus, with the Atlantic salmon virus, PMCV, as its closest relative.

Accordingly, one aspect of the invention provides a nucleic acid comprising at least one open reading frame (ORF) sequence selected from the group consisting of ORF-1, ORF-2, ORF-X, ORF-Y and ORF-Z; wherein
   ORF-1 is at least 80% identical to the nucleic acid sequence of SEQ ID NO:1,
   ORF-2 is at least 80% identical to the nucleic acid sequence of SEQ ID NO:2,
   ORF-X is at least 80% identical to the nucleic acid sequence of SEQ ID NO:3,
   ORF-Y is at least 80% identical to the nucleic acid sequence of SEQ ID NO:4, and
   ORF-Z is at least 80% identical to the nucleic acid sequence of SEQ ID NO:5.

Another aspect of the invention provides a nucleic acid, wherein (a) the sequence of said nucleic acid is complementary to SEQ ID NO: 1 and/or to SEQ ID NO: 2; and/or (b) the sequence of said nucleic acid is complementary to SEQ ID NO: 6.

Another aspect of the invention provides a viral polypeptide comprising an amino acid sequence that is at least 80%, at least 90%, or at least 95% identical to any one of SEQ ID NOs 7-11, or that is any one of SEQ ID NOs 7-11 or a conservatively substituted variant thereof.

Another aspect of the invention provides a virus that infects and is capable of killing lumpsucker fish (*Cyclopterus lumpus*), wherein the virus genome comprises a nucleic acid sequence disclosed herein, wherein said nucleic acid sequence contains the base uracil (U) instead of the base thymine (T), and/or wherein the virus comprises a viral polypeptide comprising an amino acid sequence that is at least 80%, at least 90%, or at least 95% identical to any one of SEQ ID NOs 7-11, or that is any one of SEQ ID NOs 7-11 or a conservatively substituted variant thereof.

Another aspect of the invention provides an oligonucleotide primer which comprises a sequence of at least 9 nucleotides, wherein said sequence is complementary to a nucleic acid sequence which is comprised within the genome of the virus disclosed herein.

Another aspect of the invention provides an oligonucleotide primer which (a) comprises a sequence of at least 9 consecutive nucleotides, wherein said sequence is complementary to a nucleic acid sequence which is comprised within the genome of the virus disclosed herein, (b) comprises at least 9 consecutive nucleotides of a sequence which is, or which is complementary to, a portion of a reference nucleic acid sequence selected from the group consisting of SEQ ID NO:1, SEQ ID NO:2, SEQ ID NO:3, SEQ ID NO: 4, SEQ ID NO:5 or SEQ ID NO:6, or (c) comprises at least 9 consecutive nucleotides of a sequence which is at least 80% identical to a sequence which is, or which is complementary to, a sequence selected from the group consisting of SEQ ID NO:12 to SEQ ID NO:40; preferably with the proviso that said oligonucleotide primer does not comprise a sequence selected from the group consisting of SEQ ID NO: 41 to SEQ ID NO:49.

Another aspect of the invention provides a method for detecting a virus that infects and is capable of killing fish, comprising the steps of:

(a) contacting a nucleic acid extracted from a biological sample of a fish with at least one oligonucleotide primer to form a mixture, wherein the at least one oligonucleotide primer is complementary to a nucleic acid sequence which is comprised within the genome of the virus disclosed herein, and (b) determining whether upon subjecting the mixture of a) to amplification an amplification product is present, wherein the presence of amplification product indicates the presence of RNA associated with the virus, and hence the presence of the virus in the biological sample.

Another aspect of the invention provides a method for detecting a virus that infects and is capable of killing fish, comprising the steps of:

(a) sequencing a nucleic acid extracted from a biological sample of a fish, and (b) comparing the resulting nucleic acid sequence with a nucleic acid sequence which is, or which is complementary to, a reference sequence selected from the group consisting of SEQ ID NO:1, SEQ ID NO:2, SEQ ID NO:3, SEQ ID NO:4, SEQ ID NO:5 and SEQ ID NO: 6, wherein an at least 80% sequence identity between the two sequences indicates the presence of the virus in the biological sample.

Another aspect of the invention provides a method for detecting a virus that infects and is capable of killing fish, comprising the steps of:

(a) sequencing a nucleic acid extracted from a biological sample of a fish, and (b) translating the resulting nucleic acid sequence into an amino acid sequence or translating a nucleic acid sequence complementary to said resulting nucleic acid sequence into an amino acid sequence, and (c) comparing the resulting amino acid sequence with a reference sequence selected from the group consisting of SEQ ID NOS 7-11, wherein an at least 80% sequence identity between the two sequences indicates the presence of the virus in the biological sample.

Another aspect of the invention provides an antibody that binds a polypeptide, wherein the polypeptide is encoded by a nucleic acid sequence which is comprised within the genome of the virus disclosed herein, and/or wherein the polypeptide comprises an amino acid sequence that is at least 80%, at least 90%, or at least 95% identical to any one of SEQ ID NOs 7-11, or that is any one of SEQ ID NOS 7-11 or a conservatively substituted variant thereof.

Another aspect of the invention provides a kit for detecting a virus in a biological sample from fish, wherein the kit comprises an oligonucleotide primer disclosed herein and/or an antibody described herein.

Another aspect of the invention provides an antibody for use in treating fish infected with a virus disclosed herein.

Another aspect of the invention provides a use of the virus disclosed herein for producing a vaccine.

Another aspect of the invention provides a vaccine comprising:

(i) a nucleic acid sequence which is comprised within the genome of the virus disclosed herein;

(ii) a nucleic acid sequence disclosed herein;

(iii) a viral polypeptide encoded by a nucleic acid sequence which is comprised within the genome of the virus disclosed herein;

(iv) a viral polypeptide comprising an amino acid sequence that is at least 80%, at least 90%, or at least 95% identical to any one of SEQ ID NOs 7-11, or that is any one of SEQ ID NOs 7-11 or a conservatively substituted variant thereof; or (v) a virus disclosed herein.

Yet another aspect of the invention provides an interfering RNA (iRNA) molecule for use in treating fish infected with a virus, wherein the iRNA molecule comprises at least 12 consecutive nucleotides of, or complimentary to, a nucleic acid sequence comprised within the genome of the virus disclosed herein.

BRIEF DESCRIPTION OF THE FIGURES

Figure 2A:
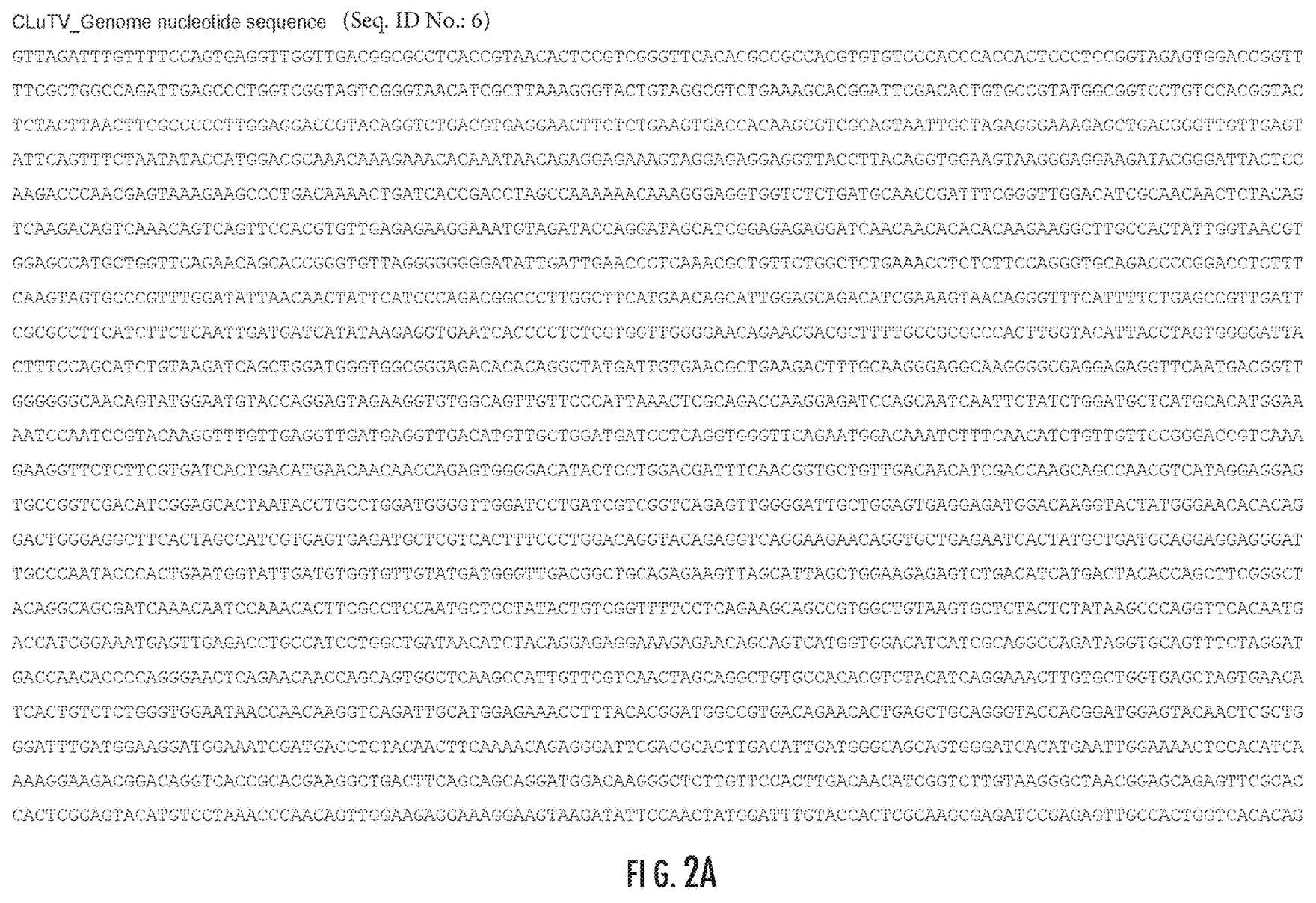
Figure 2B:
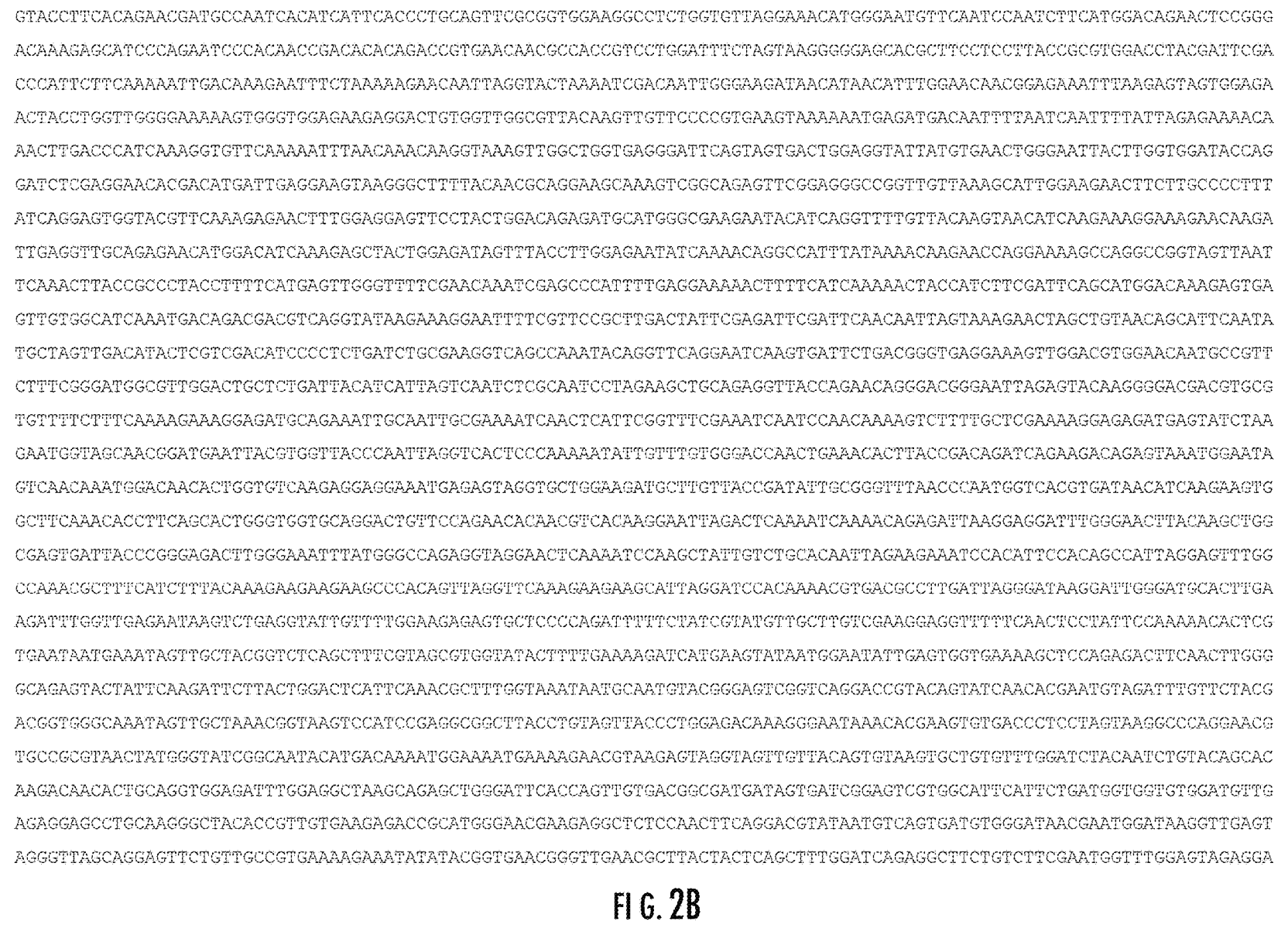

FIG. 2A through 2C: CLuTV genome nucleotide sequence.

FIG. 3: CLuTV ORF-1 nucleotide sequence.

FIG. 4: CLuTV ORF-2 nucleotide sequence.

FIG. 5: CLuTV ORF-X, ORF-Y and ORF-Z nucleotide sequences.

FIG. 6: CLuTV ORF-1 amino acid sequence.

FIG. 7: CLuTV ORF-2 amino acid sequence.

FIG. 8: CLuTV ORF-X, ORF-Y and ORF-Z amino acid sequences.

DETAILED DESCRIPTION OF THE INVENTION

Definitions

Figure 1:
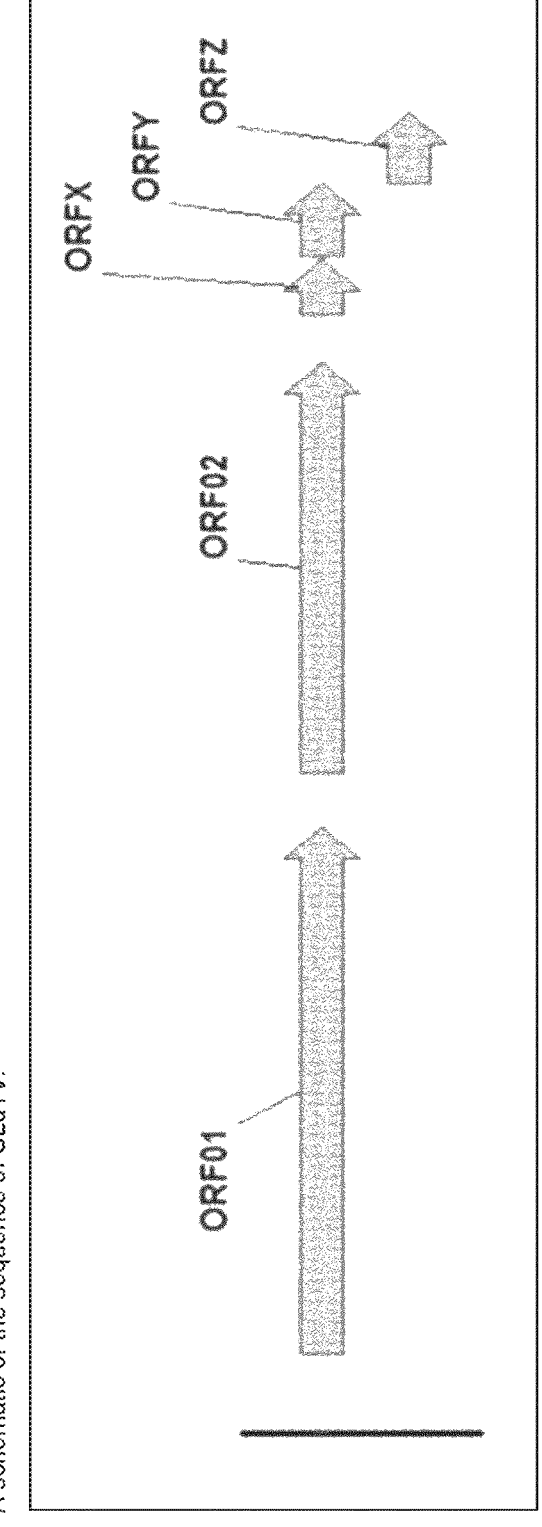
FIG. 1: A schematic of the sequence of CLuTV identified herein, which is 6,353 nucleotides long and contains five possible open reading frames (ORFs).

In order for the present invention to be readily understood, several definitions of terms used in the course of the invention are set forth below.

As used herein, the term "lumpsucker" or "lumpfish" is intended to mean any species selected from the whole family of Cyclopteridae. The most preferred species according to the invention is *Cyclopterus lumpus.*

The term "nucleic acid" includes DNA molecules (e.g., cDNA or genomic DNA), RNA molecules (e.g., mRNA), analogues of DNA or RNA generated using nucleotide analogues (e.g., peptide nucleic acids and non-naturally occurring nucleotide analogues), and hybrids thereof. Thus, whereas the nucleic acid sequences provided in FIGS. 2 to 5 and SEQ ID NOs: 1 to 6 use the bases guanine, cytosine, adenine and thymine, embodiments of the invention relate to their corresponding RNA sequences which use the bases guanine, cytosine, adenine and uracil (i.e., with uracil instead of thymine), which RNA sequences are therefore also provided herein. The nucleic acid molecule can be single-stranded or double-stranded. Unless specified otherwise, the left-hand end of any single-stranded nucleic acid sequence discussed herein is the 5' end. The direction of 5' to 3' addition of nascent RNA transcripts is the transcription direction.

The term "oligonucleotide" means a nucleic acid comprising 200 or fewer nucleotides. Oligonucleotides can be single stranded, e.g., for use as primers, cloning primers or hybridization probes, or they can be double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays.

As used herein, the term "oligonucleotide primer" or "primer" is to be understood to refer to a nucleic acid sequence (e.g., of at least 9 nucleotides in length, and less than 60 nucleotides in length) suitable for directing an activity to a region of a nucleic acid, e.g. for amplification of a target nucleic acid sequence by the polymerase chain reaction (PCR), or for in situ hybridization.

As used herein, the term "complementary" in the context of nucleic acid sequences means nucleic acid sequences that form a double-stranded structure by matching base pairs (A to T (or U) and G to C). For example, the complementary nucleic acid sequence to G-T-A-C is C-A-T-G. Other examples of complementary nucleic acid sequences are the following:

Complementary nucleic acid sequence (e.g., in case the nucleic acid is DNA):

```
5'-ATTCGCTTAACGCAA-3'

3'-TAAGCGAATTGCGTT-5'
```

The corresponding complementary sequences wherein uracil is substituted for thymine (e.g., in case the nucleic acid is RNA):

```
5'-AUUCGCUUAACGCAA-3'

3'-UAAGCGAAUUGCGUU-5'
```

As used herein, the term "amino acid" refers to one of the 20 naturally occurring amino acids or any non-natural analogues. Preferably, the term "amino acid" refers to one of the 20 naturally occurring amino acids.

The terms "polypeptide" or "protein" mean a macromolecule composed of a sequence of amino acids. A protein can be a native protein, that is, a protein produced by a naturally-occurring and non-recombinant cell; or it can be produced by a genetically-engineered or recombinant cell, and comprise molecules having the amino acid sequence of the native protein, or molecules having deletions from, additions to, and/or substitutions of one or more amino acids of the native sequence. The terms also include amino acid polymers in which one or more amino acids are chemical analogues of a corresponding naturally-occurring amino acid polymer.

The term "sequence identity" indicates a quantitative measure of the degree of homology between two sequences, which can be nucleic acid (also termed nucleotide) sequences or amino acid sequences. If the two sequences to be compared are not of equal length, they must be aligned to give the best possible fit, allowing the insertion of gaps or alternatively, truncation at the ends of the nucleic acid sequences or amino acid sequences.

In the case of a nucleotide sequence, for example, the term "at least 80% identical" thus means that at least 80% of the nucleotides over the entire sequence can be aligned with identical nucleotides from another sequence. A specified percentage of nucleotides can be referred to as e.g. 80% identical, 85% identical, 90% identical, 95% identical, 99% identical or more over a specified region when compared and aligned for maximum correspondence. For example, a sequence which is 10 nucleotides in length, say GGGAAACCTT, can be 80% identical with a continuous sequence (e.g., GGGAAACCGG), or with a non-continuous sequence (e.g., GGGACCCCTT):

100% Identity Example:

```
GGGAAACCTT
||||||||||
GGGAAACCTT
```

80% Identity Example:

```
GGGAAACCTT
||||||||
GGGAAACCGG
```

80% Identity Example:

```
GGGAAACCTT
||||  ||||
GGGACCCCTT
```

The skilled person will acknowledge that various means for comparing sequences are available (see below).

As used herein, the term "conservatively substituted" in reference to an amino acid means that the amino acid can be substituted by another amino acid in its respective group, according to the following six groups: [1] Alanine (A), Serine(S), Threonine (T); [2] Aspartic acid (D), Glutamic acid (E); [3] Asparagine (N), Glutamine (Q); [4] Arginine (R), Lysine (K); [5] Isoleucine (I), Leucine (L), Methionine (M), Valine (V); and [6] Phenylalanine (F), Tyrosine (Y), Tryptophan (W). A "conservatively substituted variant" in reference to a polypeptide or protein means that any of the amino acids in said polypeptide or protein can be conservatively substituted as defined hereinabove.

As used herein, the term "antibody" refers to a glycoprotein comprising at least two heavy (H) chains and two light (L) chains inter-connected by disulfide bonds, or an antibody fragment (antigen binding portion) thereof. Each heavy chain is comprised of a heavy chain variable region (VH) and a heavy chain constant region (CH). The heavy chain constant region is comprised of three domains, CH1, CH2 and CH3. Each light chain is comprised of a light chain variable region (VL) and a light chain constant region (CL). The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host cells or factors, including various cells of the immune system (e.g., effector cells) and the first component (C1q) of the classical complement system. Antibodies of the invention include monoclonal antibodies (including full length monoclonal antibodies) and polyclonal antibodies, whole antibodies, chimeric antibodies, humanized antibodies, human antibodies or hybrid antibodies with dual or multiple antigen or epitope specificities, antibody fragments and antibody sub-fragments, e.g., Fab, Fab', $F(ab')_2$, fragments and the like, including hybrid fragments of any immunoglobulin or any natural, synthetic or genetically engineered protein that acts like an antibody by binding to a specific antigen to form a complex. Antibodies of the invention can also be Fc fusion proteins.

A "vector" is a nucleic acid that can be used to introduce another nucleic acid (or "construct") linked to it into a cell. One type of vector is a "plasmid", which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) integrate into the genome of a host cell upon introduction into the host cell and culturing under selective pressure, and thereby are replicated along with the host genome. A vector can be used to direct the expression of a chosen nucleic acid in a cell.

A "host cell" is a cell that can be used to express a nucleic acid, e.g., a nucleic acid disclosed herein. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Exemplary host cells include Chinese hamster ovary (CHO) cell lines or their derivatives.

Typically, a host cell is a cultured cell that can be transformed or transfected with a polypeptide-encoding nucleic acid, which can then be expressed in the host cell. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The terms "treat" and "treatment" include therapeutic treatments, prophylactic treatments, and applications which reduce symptoms of a disorder or reduce the risk that a subject (e.g., a fish) will develop a disorder (e.g., symptoms of virus infection).

The term "vaccine" as used herein refers to a material that can produce an immune response that blocks the infectivity, either partially or fully, of an infectious agent, which in respect of the present invention is the virus affecting fish, e.g., lumpsuckers. Thus, when administering to a fish, the vaccine of the invention immunises the fish against the disease caused by the virus. The immunising component of the vaccine may be, e.g., DNA as in a DNA vaccine, RNA as in a RNA vaccine, a recombinant protein or fragment thereof according to the present invention, or a live or attenuated recombinant virus.

An "iRNA agent" (abbreviation for "interfering RNA agent") as used herein, is an RNA agent which can down-regulate (reduce) the expression of a target gene, e.g., a protein encoded by ORF-1, ORF-2, ORF-X, ORF-Y or ORF-Z. An iRNA agent may act by one or more mechanisms, including post-transcriptional cleavage of a target mRNA sometimes referred to in the art as "RNAi", or pre-transcriptional or pre-translational mechanisms. An iRNA agent can be a double-stranded (ds) IRNA agent. An iRNA agent can also be a "small interfering RNA" (siRNA).

The terms "of the invention" or "according to the invention" as used herein are intended to refer to all aspects and embodiments of the invention disclosed and/or claimed herein. Conversely, any aspects, items or embodiments referred to herein as being "disclosed herein" or "described herein" are to be understood as being aspects, items or embodiments "of the invention" or "according to the invention".

As used herein, the term "comprising" is to be construed as encompassing both "including" and "consisting of", both meanings being specifically intended, and hence individually disclosed, embodiments according to the present invention.

As used herein, the articles "a" and "an" preceding an element or component are intended to be nonrestrictive regarding the number of instances (i.e. occurrences) of the element or component. Therefore, "a" or "an" is to be read to include one or at least one, and the singular word form of the element or component also includes the plural unless the number is obviously meant to be singular.

As used herein, the term "about" modifying the quantity of a substance, ingredient, component, or parameter employed refers to variation in the numerical quantity that can occur, for example, through typical measuring and handling procedures, e.g., liquid handling procedures used for making concentrates or solutions. Furthermore, variation can occur from inadvertent error in measuring procedures, differences in the manufacture, source, or purity of the ingredients employed to carry out the methods, and the like. In one embodiment, the term "about" means within 10% of the reported numerical value. In a more specific embodiment, the term "about" means within 5% of the reported numerical value.

Virus Nucleic Acid Sequences and Viral Polypeptides

One aspect of the invention provides a nucleic acid comprising at least one open reading frame (ORF) sequence selected from the group consisting of ORF-1, ORF-2, ORF-X, ORF-Y and ORF-Z; wherein ORF-1 is at least 80% identical to the nucleic acid sequence of SEQ ID NO:1, ORF-2 is at least 80% identical to the nucleic acid sequence of SEQ ID NO:2, ORF-X is at least 80% identical to the nucleic acid sequence of SEQ ID NO:3, ORF-Y is at least 80% identical to the nucleic acid sequence of SEQ ID NO:4, and ORF-Z is at least 80% identical to the nucleic acid sequence of SEQ ID NO:5.

In some embodiments,

ORF-1 is at least 85% identical to the nucleic acid sequence of SEQ ID NO:1,

ORF-2 is at least 85% identical to the nucleic acid sequence of SEQ ID NO:2,

ORF-X is at least 85% identical to the nucleic acid sequence of SEQ ID NO:3,

ORF-Y is at least 85% identical to the nucleic acid sequence of SEQ ID NO:4, and ORF-Z is at least 85% identical to the nucleic acid sequence of SEQ ID NO:5.

In preferred embodiments,

ORF-1 is at least 90% identical to the nucleic acid sequence of SEQ ID NO:1,

ORF-2 is at least 90% identical to the nucleic acid sequence of SEQ ID NO:2,

ORF-X is at least 90% identical to the nucleic acid sequence of SEQ ID NO:3,

ORF-Y is at least 90% identical to the nucleic acid sequence of SEQ ID NO:4, and ORF-Z is at least 90% identical to the nucleic acid sequence of SEQ ID NO:5.

In more preferred embodiments,

ORF-1 is at least 95% identical to the nucleic acid sequence of SEQ ID NO:1,

ORF-2 is at least 95% identical to the nucleic acid sequence of SEQ ID NO:2,

ORF-X is at least 95% identical to the nucleic acid sequence of SEQ ID NO:3,

ORF-Y is at least 95% identical to the nucleic acid sequence of SEQ ID NO:4, and ORF-Z is at least 95% identical to the nucleic acid sequence of SEQ ID NO:5.

In yet more preferred embodiments,

ORF-1 is at least 98% identical to the nucleic acid sequence of SEQ ID NO:1,

ORF-2 is at least 98% identical to the nucleic acid sequence of SEQ ID NO:2,

ORF-X is at least 98% identical to the nucleic acid sequence of SEQ ID NO:3,

ORF-Y is at least 98% identical to the nucleic acid sequence of SEQ ID NO:4, and ORF-Z is at least 98% identical to the nucleic acid sequence of SEQ ID NO:5.

In yet even more preferred embodiments,

ORF-1 is at least 99% identical to the nucleic acid sequence of SEQ ID NO:1,

ORF-2 is at least 99% identical to the nucleic acid sequence of SEQ ID NO:2,

ORF-X is at least 99% identical to the nucleic acid sequence of SEQ ID NO:3,

ORF-Y is at least 99% identical to the nucleic acid sequence of SEQ ID NO:4, and ORF-Z is at least 99% identical to the nucleic acid sequence of SEQ ID NO:5.

In particularly preferred embodiments,

ORF-1 is the nucleic acid sequence of SEQ ID NO:1,

ORF-2 is the nucleic acid sequence of SEQ ID NO:2,

ORF-X is the nucleic acid sequence of SEQ ID NO:3,

ORF-Y is the nucleic acid sequence of SEQ ID NO:4, and

ORF-Z is the nucleic acid sequence of SEQ ID NO:5.

In particular embodiments, the nucleic acid disclosed herein comprises at least ORF-1 and/or ORF-2, according to any of their embodiments disclosed herein.

The sequence of the nucleic acid disclosed herein can be at least 80% identical to the virus genome according to SEQ ID NO:6. In some embodiments, the sequence of the nucleic acid disclosed herein is at least 85% identical to the virus genome according to SEQ ID NO:6. In preferred embodiments, the sequence of the nucleic acid disclosed herein is at least 90% identical to the virus genome according to SEQ ID NO:6. In more preferred embodiments, the sequence of the nucleic acid disclosed herein is at least 95% identical to the virus genome according to SEQ ID NO:6. In yet more preferred embodiments, the sequence of the nucleic acid disclosed herein is at least 98% identical to the virus genome according to SEQ ID NO:6. In yet even more preferred embodiments, the sequence of the nucleic acid disclosed herein is at least 99% identical to the virus genome according to SEQ ID NO:6. In particularly preferred embodiments, the sequence of the nucleic acid disclosed herein has 100% identity to the sequence of the virus genome according to SEQ ID NO:6 (CLuTV).

Also provided herein is a nucleic acid the sequence of which is complementary to the sequence of any of the nucleic acids disclosed herein.

The sequence of said nucleic acid can be complementary to ORF-1, ORF-2, ORF-X, ORF-Y or ORF-Z, according to any of their embodiments disclosed herein. The sequence of the nucleic acid can also be complementary to a nucleic acid sequence which is at least 80% identical to, in some embodiments at least 85% identical to, in preferred embodiments at least 90% identical to, in more preferred embodiments at least 95% identical to, in yet more preferred embodiments 98% identical to, in yet even more preferred embodiments at least 99% identical to, and in particularly preferred embodiments 100% identical to the sequence of the virus genome according to SEQ ID NO:6 (CLuTV).

Accordingly, the invention also provides a nucleic acid, wherein (a) the sequence of said nucleic acid is complementary to any one of SEQ ID NO: 1 to SEQ ID NO: 5; and/or (b) the sequence of said nucleic acid is complementary to SEQ ID NO: 6.

Accordingly, the invention also provides a nucleic acid, wherein (a) the sequence of said nucleic acid is complementary to SEQ ID NO: 1 and/or to SEQ ID NO: 2; and/or (b) the sequence of said nucleic acid is complementary to SEQ ID NO: 6.

In preferred embodiments, the nucleic acid sequences disclosed herein are RNA nucleic acid sequences, i.e., they contain the base uracil (U) instead of the base thymine (T). Accordingly, the viruses disclosed herein contain their genetic information in the form of such RNA nucleic acid sequences.

The skilled person will further acknowledge that alterations of the nucleic acid sequence resulting in modifications of the amino acid sequence of the protein it codes may have little, if any, effect on the resulting three dimensional structure of the protein. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in the substitution of one negatively charged residue for another, such as aspartic acid for glutamic acid, or one positively charged residue for another, such as lysine for arginine, can also be expected to produce a protein with substantially the same functional activity. The following six groups each contain amino acids that are typical conservative substitutions for one another: [1] Alanine (A), Serine(S), Threonine (T); [2] Aspartic acid (D), Glutamic acid (E); [3] Asparagine (N), Glutamine (Q); [4] Arginine (R), Lysine (K); [5] Isoleucine (I), Leucine (L), Methionine (M), Valine (V); and [6] Phenylalanine (F), Tyrosine (Y), Tryptophan (W), (see, e.g., US Patent Publication 20100291549).

Preferably, ORF-1, ORF-2, ORF-X, ORF-Y and ORF-Z encode viral polypeptides comprising amino acid sequences of SEQ ID NOS: 7-11, respectively, or amino acid sequences that are at least 80% identical (e.g., at least 85% identical or at least 90% identical, or at least 91% identical, at least 92% identical, at least 93% identical, at least 94% identical, at least 95% identical, at least 96% identical, at least 97% identical, at least 98% identical, or at least 99% identical) to amino acid sequences SEQ ID NOs: 7-11, respectively. In certain embodiments, ORF-1, ORF-2, ORF-X, ORF-Y and ORF-Z encode viral polypeptides that are conservatively substituted variants of SEQ ID NOs 7-11, respectively, as described above.

Therefore, in another aspect, herein provided are viral polypeptides comprising amino acid sequences of SEQ ID NOS: 7-11, respectively, or amino acid sequences that are at least 80% identical (e.g., at least 85% identical or at least 90% identical, or at least 91% identical, at least 92% identical, at least 93% identical, at least 94% identical, at least 95% identical, at least 96% identical, at least 97% identical, at least 98% identical, or at least 99% identical) to amino acid sequences SEQ ID NOs: 7-11, respectively. In certain embodiments, the viral polypeptides are conservatively substituted variants of SEQ ID NOs 7-11, respectively, as described above. Vectors, e.g., plasmid vectors or viral vectors, comprising nucleic acid sequences encoding the viral polypeptides of the invention as described above, are also provided.

Protein and/or nucleic acid sequence identities (homologies) can be evaluated using any of the variety of sequence comparison algorithms and programs known in the art. For sequence comparison, typically one sequence acts as a reference sequence (e.g., a sequence disclosed herein), to which test sequences are compared. A sequence comparison algorithm then calculates the percent sequence identities for the test sequences relative to the reference sequence, based on the program parameters.

The percent identity of two amino acid or two nucleic acid sequences can be determined for example by comparing sequence information using the computer program GAP, i.e., Genetics Computer Group (GCG; Madison, WI) Wisconsin package version 10.0 program, GAP (Devereux et al. (1984), Nucleic Acids Res. 12:387-95). In calculating percent identity, the sequences being compared are typically aligned in a way that gives the largest match between the sequences. The preferred default parameters for the GAP program include: (1) The GCG implementation of a unary comparison matrix (containing a value of 1 for identities and 0 for non-identities) for nucleotides, and the weighted amino acid comparison matrix of Gribskov and Burgess, ((1986)

Nucleic Acids Res. 14:6745) as described in *Atlas of Polypeptide Sequence and Structure*, Schwartz and Dayhoff, eds., National Biomedical Research Foundation, pp. 353-358 (1979) or other comparable comparison matrices; (2) a penalty of 8 for each gap and an additional penalty of 2 for each symbol in each gap for amino acid sequences, or a penalty of 50 for each gap and an additional penalty of 3 for each symbol in each gap for nucleotide sequences; (3) no penalty for end gaps; and (4) no maximum penalty for long gaps.

Sequence identity and/or similarity can also be determined by using the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (BESTFIT, FASTA, and TFASTA in the Wisconsin Genetics Software Package, Genetics Computer Group, 575 Science Drive, Madison, Wis.).

Another example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, *CABIOS* 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215:403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program obtained from Altschul et al., 1996, *Methods in Enzymology* 266:460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; $X_u$ set to 16, and $X_g$ set to 40 for database search stage and to 67 for the output stage of the algorithms. Gapped alignments are triggered by a score corresponding to about 22 bits.

Methods for making the viral polypeptides described herein are well known to people of ordinary skill in the art. For example and without limitations, nucleic acid sequences encoding the viral polypeptides comprising SEQ ID NOS 7-11 or sequences at least 80% identical thereto, including conservatively substituted variants of SEQ ID NOs 7-11, may be cloned into a vector, such as, for example, a plasmid or a viral vector, and expressed in a suitable host such as fish cells, mammalian cells, bacterial cells, plant cells, and insect cells, and the expressed viral polypeptides separated therefrom.

Viruses

Another aspect of the invention provides a virus that infects and is capable of killing lumpsucker fish (*Cyclopterus lumpus*), wherein the virus genome comprises a nucleic acid sequence disclosed herein, wherein said nucleic acid sequence contains the base uracil (U) instead of the base thymine (T).

Another aspect of the invention provides a virus that infects and is capable of killing lumpsucker fish (*Cyclopterus lumpus*), wherein the virus comprises a viral polypeptide comprising an amino acid sequence that is at least 80%, at least 90%, or at least 95% identical to any one of SEQ ID NOs 7-11, or that is any one of SEQ ID NOs 7-11 or a conservatively substituted variant thereof.

Another aspect of the invention provides a virus that infects and is capable of killing lumpsucker fish (*Cyclopterus lumpus*), wherein the virus genome comprises a nucleic acid sequence disclosed herein, wherein said nucleic acid sequence contains the base uracil (U) instead of the base thymine (T), and wherein the virus comprises a viral polypeptide comprising an amino acid sequence that is at least 80%, at least 90%, or at least 95% identical to any one of SEQ ID NOs 7-11, or that is any one of SEQ ID NOs 7-11 or a conservatively substituted variant thereof.

In preferred embodiments, the nucleic acid comprised within the virus is in the form of double-stranded RNA (dsRNA).

In some embodiments, the virus genome comprises a nucleic acid sequence comprising at least one of ORF-1, ORF-2, ORF-X, ORF-Y or ORF-Z, according to any of their embodiments disclosed herein. In preferred embodiments, the sequence of the virus genome comprises at least ORF-1 and ORF-2, according to any of their embodiments disclosed herein. In some embodiments, the virus genome comprises a nucleic acid sequence which is, or which is complementary to, a nucleic acid sequence which is at least 80%, preferably at least 85%, more preferably at least 90%, even more preferably at least 95%, yet even more preferably 98%, particularly preferably 99%, or even 100% identical to the sequence of the virus genome according to SEQ ID NO:6 (CLuTV).

In some embodiments, the virus comprises ORF-1, ORF-2, ORF-X, ORF-Y and ORF-Z; wherein ORF-1 is at least 80% identical to the nucleic acid sequence of SEQ ID NO:1, ORF-2 is at least 80% identical to the nucleic acid sequence of SEQ ID NO:2, ORF-X is at least 80% identical to the nucleic acid sequence of SEQ ID NO:3, ORF-Y is at least 80% identical to the nucleic acid sequence of SEQ ID NO:4, and ORF-Z is at least 80% identical to the nucleic acid sequence of SEQ ID NO:5;

and wherein ORF-1, ORF-2, ORF-X, ORF-Y and ORF-Z encode viral polypeptides comprising SEQ ID NOs 7-11, respectively, or sequences that are at least 80% identical to SEQ ID NOs 7-11, respectively.

In some embodiments, the genome of the virus encodes viral polypeptides comprising respective amino acid sequences comprising SEQ ID NOs 7-11 or sequences at least 80% identical thereto (for example, at least 85%, at least 90%, at least 91%, at least 92%, at least 93%, at least 94%, at least 95%, at least 96%, at least 97%, at least 98%, or at least 99% identical to SEQ ID NOs 7-11). Preferably, the virus comprises ORF-1, ORF-2, ORF-X, ORF-Y and ORF-Z as defined herein, wherein said ORF-1, ORF-2, ORF-X, ORF-Y and ORF-Z encode viral polypeptides that are at least 95% identical to SEQ ID NOs 7-11, respectively. More preferably, the virus comprises ORF-1, ORF-2, ORF-X, ORF-Y and ORF-Z as defined herein, wherein said ORF-1, ORF-2, ORF-X, ORF-Y and ORF-Z encode viral polypeptides that are conservatively substituted variants of SEQ ID NOS 7-11, respectively, or viral polypeptides comprising the amino acid sequences of SEQ ID NOs 7-11, respectively.

In certain embodiments, the genome of the virus encodes at least SEQ ID NOs 7 and 8, or sequences that are at least 80% identical thereto (for example, at least 85%, at least 90%, at least 91%, at least 92%, at least 93%, at least 94%, at least 95%, at least 96%, at least 97%, at least 98%, or at least 99%), including conservatively substituted variants of SEQ ID NOs 7 and 8.

In some embodiments, the infection of lumpsucker fish by the virus disclosed herein causes the following symptoms in the fish:

(i) tissue damage in the intestine, and/or (ii) diarrhoea; or (iii) cardiomyopathy.

In preferred embodiments, the infection of lumpsucker fish by the virus disclosed herein causes cardiomyopathy.

Tissue damage in the intestine can be diagnosed by the use of histology or electron microscopy to observe destruction of intestinal tissue, for example, destruction of the structure of villi, increased thickness of other layers. Preferably, tissue sections are stained using a Haematoxylin and Eosin (H&E) histological stain. In employing such a stain, infected individuals can be observed with accumulation of fluids and undigested feed particles in both the stomach and the intestine (see, e.g., FIGS. 9 to 12), leading to a diarrhoea-like condition in these fish. In addition, damage to the intestinal wall, with cellular discharge and increased mucus production can be observed (see, e.g., FIGS. 10 to 12). Fish diarrhoea can be observed in the water tanks of the farmed fish.

Changes in bio-macromolecule components (proteins in general, siderophile proteins, neutral mucopolysaccharides, glycogen and acid mucopolysaccharides) can also be observed in intestinal tissue samples by conventional methods, e.g., Western blotting, ELISA, staining of tissue sections, etc.

Cardiomyopathy can be diagnosed by histopathology, with severe inflammation and degeneration of the spongious part of the myocardium (ventricle) and with similar changes in the atrium, again preferably using a Haematoxylin and Eosin (H&E) histological stain. Myocyte degeneration and inflammatory changes are not frequently seen in the compact layer of the heart and always occur later than changes of the spongious parts. Circulatory disturbance with multifocal liver necrosis may also occur. Fish suffering from CMS may show symptoms such as abnormal swimming behaviour. At autopsy, findings include cardiac tamponade with blood in the pericardial sac and moderate to pronounced ascites (Haugland et al, J. Virol, 85, 2011).

In some embodiments, the virus is a non-enveloped virus. In contrast to enveloped viruses, non-enveloped viruses are characterised by a higher resistance to chemical and physical forces, e.g., they are heat-resistant.

In preferred embodiments, the virus is a Totivirus. Such viruses are non-enveloped, with icosahedral symmetry, and T=2 architecture. The diameter is typically around 40 nm.

In some embodiments, the virus disclosed herein comprises a 5' untranslated region (5' UTR) which functions as an internal ribosome entry site (IRES).

In preferred embodiments, ORF-1 and ORF-2 code for a capsid protein (CP) and an RNA-dependent RNA polymerase (RDRP).

Also provided herein is a vector comprising a nucleic acid that encodes at least one ORF, as disclosed herein with all their embodiments. In some embodiments, the vector comprises a nucleic acid that encodes the complete virus disclosed herein. The vector can be used to introduce said nucleic acid(s) into a cell, such as a host cell.

Also provided herein is a host cell comprising the virus described herein. The host cell may be a bacterial cell, a fish cell or a mammalian cell.

Oligonucleotide Primers

Another aspect of the invention provides an oligonucleotide primer which comprises a sequence of at least 9 nucleotides, wherein said sequence is complementary to a nucleic acid sequence which is comprised within the genome of the virus disclosed herein.

Another aspect of the invention provides an oligonucleotide primer which (a) comprises a sequence of at least 9 consecutive nucleotides, wherein said sequence is complementary to a nucleic acid sequence which is comprised within the genome of the virus disclosed herein, (b) comprises at least 9 consecutive nucleotides of a sequence which is, or which is complementary to, a portion of a reference nucleic acid sequence selected from the group consisting of SEQ ID NO:1, SEQ ID NO:2, SEQ ID NO:3, SEQ ID NO: 4, SEQ ID NO:5 or SEQ ID NO:6, or (c) comprises at least 9 consecutive nucleotides of a sequence which is at least 80% identical to a sequence which is, or which is complementary to, a sequence selected from the group consisting of SEQ ID NO: 12 to SEQ ID NO:40; preferably with the proviso that said oligonucleotide primer does not comprise a sequence selected from the group consisting of SEQ ID NO: 41 to SEQ ID NO:49.

In some embodiments, the oligonucleotide primer is 9 to 60 nucleotides in length. In preferred embodiments, the oligonucleotide primer is 12 to 40 nucleotides in length. In more preferred embodiments, the oligonucleotide primer is 15 to 30 nucleotides in length. In even more preferred embodiments, the oligonucleotide primer is 18 to 25 nucleotides in length.

As the skilled person will readily appreciate, an oligonucleotide primer which is complementary to a nucleic acid sequence will hybridize to that sequence under stringent conditions. The "stringent conditions" refer to conditions of temperature, ionic strength, and the presence of other compounds such as organic solvents, under which nucleic acid hybridizations are conducted. Under stringent conditions, nucleic acid base pairing will occur only between nucleic acid sequences having a high frequency of complementary bases. Stringent hybridization conditions are known to the skilled person (see e.g. Green M. R., Sambrook, J., Molecular Cloning: A Laboratory Manual, Cold Spring Harbor Laboratory Press; 4th edition, 2012). The precise conditions for stringent hybridization are typically sequence-dependent and will be different in different circumstances, as the skilled person will readily appreciate. Longer sequences hybridize at higher temperatures compared to shorter sequences. Generally, stringent conditions are selected to be about 5° C. lower than the thermal melting point (Tm) for the specific sequence. The Tm is defined as the temperature when 50% of the duplex molecules have dissociated into their constituent single strands. Since the target sequences are generally present at excess, at Tm, 50% of nucleic acid primers would generally be occupied at equilibrium. Typically, stringent conditions will be those in which the salt concentration is less than about 1.0 M sodium ions, typically about 0.01 to 1.0 M sodium ions (or other salts) at pH 6.8 to 8.3 and the temperature is at least about 30° C. for short primers (e.g., 10 nucleotides to 50 nucleotides) and at least about 60° C. for longer primers. Stringent conditions may also be achieved with the addition of destabilizing agents, such as formamide. As the skilled person will readily appreciate, due to sequence complementarity of the sequences, the oligonucleotide primer according to the invention therefore hybridizes to a nucleic acid sequence which is comprised within the genome of the virus disclosed herein.

An oligonucleotide primer according to the present invention may be labelled with a molecular marker in order to enable visualization of hybridization to target sequence or quantification of amplification of target sequence. Various molecular markers or labels are known to the skilled person.

In a particular embodiment, herein provided is an oligonucleotide primer which comprises at least 9 consecutive nucleotides of a sequence which is, or which is complementary to, a portion (e.g., 9 to 60 nucleotides in length, preferably 12 to 40 nucleotides in length, more preferably 15 to 30 nucleotides in length, even more preferably 18 to 25 nucleotides in length) of a reference nucleic acid sequence selected from the group consisting of SEQ ID NO:1, SEQ ID NO:2, SEQ ID NO:3, SEQ ID NO:4, SEQ ID NO: 5 or SEQ ID NO:6; preferably with the proviso that said oligonucleotide primer does not comprise a sequence selected from the group consisting of SEQ ID NO:41 to SEQ ID NO:49. In a particularly preferred embodiment, the sequence of said oligonucleotide primer consists of said sequence of consecutive nucleotides.

In another particular embodiment, herein provided is an oligonucleotide primer which comprises at least 9 (preferably at least 12, more preferably at least 15, even more preferably at least 18) consecutive nucleotides of a sequence which is at least 80% identical to a sequence which is, or which is complementary to, a sequence selected from the group consisting of SEQ ID NO:12 to SEQ ID NO:40; preferably with the proviso that said oligonucleotide primer does not comprise a sequence selected from the group consisting of SEQ ID NO:41 to SEQ ID NO:49.

Another aspect of the invention provides a use of at least one oligonucleotide primer in a method of detecting the virus disclosed herein, wherein the at least one primer comprises a sequence of at least 9 nucleotides, e.g., 9 consecutive nucleotides, (preferably at least 12, more preferably at least 15, even more preferably at least 18) and wherein said sequence is complementary to a nucleic acid sequence which is comprised within the genome of said virus.

In some embodiments, the at least one oligonucleotide primer is a primer pair, i.e., two primers, one forward primer and one reverse primer, which are complementary to two regions on a nucleic acid sequence, and which can be used to amplify a sequence between said two regions. This is well known to a skilled person, and it is within his/her skills to find oligonucleotide primers suitable to constitute a pair. According to the use of the invention, a "primer pair" can be used to amplify a nucleic acid sequence which is comprised within the genome of the virus described herein.

In some embodiments, the use employs cDNA synthesis in a method of detecting the virus disclosed herein. For example, random oligonucleotide primers (e.g., hexanucleotides) are used to synthesize cDNAs from a nucleic acid sequence which is comprised within the genome of said virus.

In some embodiments, the use employs PCR in a method of detecting the virus disclosed herein. In some embodiments, the use employs RT-PCR in a method of detecting the virus disclosed herein. In some embodiments, the use employs RT-qPCR in a method of detecting the virus disclosed herein. In some embodiments, the use employs Random Multiplex RT-PCR in a method of detecting the virus disclosed herein; this method uses a mixture of primers designed to be resistant to primer-dimer amplification (see Clem et al, Virol J, 4, 2007). In some embodiments, the use employs transcription mediated amplification (TMA) in a method of detecting the virus disclosed herein. In some embodiments, the use employs strand displacement amplification (SDA) in a method of detecting the virus disclosed herein.

In some embodiments, the use employs in situ detection, also termed in situ hybridization (ISH) in a method of detecting the virus disclosed herein, for example fluorescence in situ hybridization (FISH). ISH uses a labelled complementary DNA, RNA or modified oligonucleotide primer sequence (probe) to enable visualization of specific nucleic acids in morphologically preserved cells and tissue sections.

The probe can be labelled with radio-, fluorescent- or antigen-labels (e.g., digoxigenin), which can then be localized and quantified in the tissue using either autoradiography, fluorescence microscopy, or immunohistochemistry, respectively.

Diagnostic Methods

Another aspect of the invention provides a method for detecting a virus that infects and is capable of killing fish, comprising the steps of:

(a) contacting a nucleic acid extracted from a biological sample of a fish with at least one oligonucleotide primer to form a mixture, wherein the at least one oligonucleotide primer is complementary to a nucleic acid sequence which is comprised within the genome of the virus disclosed herein, and (b) determining whether upon subjecting the mixture of a) to amplification an amplification product is present, wherein the presence of amplification product indicates the presence of RNA associated with the virus, and hence the presence of the virus in the biological sample.

In some embodiments, the nucleic acid in step (a) of the method, for example RNA, is extracted from biological samples by using solid-phase extraction, e.g., on-column purification using a solid phase of silica gel membrane. In some embodiments, nucleic acid in step (a) of the method, for example RNA, is extracted from biological samples by using phenol/chloroform extraction.

The method may use any suitable oligonucleotide primer disclosed herein. Generally, the at least one oligonucleotide primer of step (a) of the method is chosen to produce an amplification product according to step (b) which has a length of 45 nucleotides to 3000 nucleotides. However, amplification products even smaller or greater in length may suitably be produced by the methods and oligonucleotide primer disclosed herein.

In some embodiments, the at least one oligonucleotide primer of step (a) of the method is chosen to produce an amplification product according to step (b) for a PCR or RT-PCR assay which has a length of 100 nucleotides to 2500 nucleotides. In preferred embodiments, the at least one oligonucleotide primer of step (a) of the method is chosen to produce an amplification product according to step (b) for a PCR or RT-PCR assay which has a length of 200 nucleotides to 1500 nucleotides. In more preferred embodiments, the at least one oligonucleotide primer of step (a) of the method is chosen to produce an amplification product according to step (b) for a PCR or RT-PCR assay which has a length of 300 nucleotides to 1000 nucleotides.

In some embodiments, the at least one oligonucleotide primer of step (a) of the method is chosen to produce an amplification product according to step (b) for a real-time RT-PCR assay which has a length of 45 nucleotides to 500 nucleotides. In preferred embodiments, the at least one oligonucleotide primer of step (a) of the method is chosen to produce an amplification product according to step (b) for a real-time RT-PCR assay which has a length of 50 nucleotides to 350 nucleotides. In more preferred embodiments, the at least one oligonucleotide primer of step (a) of the method is chosen to produce an amplification product according to step (b) for a real-time RT-PCR assay which has a length of 55 nucleotides to 250 nucleotides.

In some embodiments, the amplification of step (b) of the method employs PCR. In some embodiments, the amplification of step (b) of the method employs RT-PCR. In some embodiments, the amplification of step (b) of the method employs RT-qPCR.

In some embodiments, the amplification product of step (b) of the method is determined by Southern blot. In some embodiments, the amplification product of step (b) of the method is determined by Northern blot. In some embodiments, the amplification product of step (b) of the method is determined by spectrophotometry. In some embodiments, the amplification product of step (b) of the method is determined by use of a DNA dye. In some embodiments, the amplification product of step (b) of the method is determined by quantifying the presence of a labelled oligonucleotide primer, for example, quantifying the presence of a fluorescently-labelled oligonucleotide primer.

Another aspect of the invention provides a method for detecting a virus that infects and is capable of killing fish, comprising the steps of:

(a) sequencing a nucleic acid extracted from a biological sample of a fish, and (b) comparing the resulting nucleic acid sequence with a nucleic acid sequence which is, or which is complementary to, a reference sequence selected from the group consisting of SEQ ID NO: 1, SEQ ID NO: 2, SEQ ID NO:3, SEQ ID NO:4, SEQ ID NO:5 and SEQ ID NO:6, wherein an at least 80% sequence identity between the two sequences indicates the presence of the virus in the biological sample.

In some embodiments, nucleic acid in step (a) of the method, for example RNA, is extracted from biological samples by using solid-phase extraction, e.g., on-column purification using a solid phase of silica gel membrane. In some embodiments, nucleic acid in step (a) of the method, for example RNA, is extracted from biological samples by using phenol/chloroform extraction.

In some embodiments, the sequencing in step (a) of the method is performed by Sanger sequencing (chain termination method). In preferred embodiments, the sequencing in step (a) of the method is performed by Next Generation Sequencing (NGS), preferably Illumina (Solexa) sequencing, Roche 454 sequencing, Ion Torrent or SOLID sequencing (Goodwin S, et al., (2016) Corning of age: Ten years of next-generation sequencing technologies. Nature reviews, Genetics, 17, 333-351).

In preferred embodiments, the sequencing in step (a) of the method provides a DNA sequence, which can be directly compared to the reference DNA sequences selected from the group consisting of SEQ ID NO: 1, SEQ ID NO: 2, SEQ ID NO:3, SEQ ID NO:4, SEQ ID NO:5 and SEQ ID NO:6.

In some embodiments, an at least 85% sequence identity between the two sequences in step (b) of the method indicates the presence of the virus in the biological sample.

In preferred embodiments, an at least 90% sequence identity between the two sequences in step (b) of the method indicates the presence of the virus in the biological sample.

In more preferred embodiments, an at least 95% sequence identity between the two sequences in step (b) of the method indicates the presence of the virus in the biological sample.

In yet more preferred embodiments, an at least 98% sequence identity between the two sequences in step (b) of the method indicates the presence of the virus in the biological sample.

In yet even more preferred embodiments, an at least 99% sequence identity between the two sequences in step (b) of the method indicates the presence of the virus in the biological sample.

In a particularly preferred embodiment, a 100% sequence identity between the two sequences in step (b) of the method indicates the presence of the virus in the biological sample.

Another aspect of the invention provides a method for detecting a virus that infects and is capable of killing fish, comprising the steps of:

(a) sequencing a nucleic acid extracted from a biological sample of a fish, and (b) translating the resulting nucleic acid sequence into an amino acid sequence or translating a nucleic acid sequence complementary to said resulting nucleic acid sequence into an amino acid sequence, and (c) comparing the resulting amino acid sequence with a reference sequence selected from the group consisting of SEQ ID NOS 7-11, wherein an at least 80% sequence identity between the two sequences indicates the presence of the virus in the biological sample.

Antibodies

Another aspect of the invention provides an antibody that binds a polypeptide, wherein the polypeptide is encoded by a nucleic acid sequence which is comprised within the genome of the virus disclosed herein, and/or wherein the polypeptide comprises an amino acid sequence that is at least 80%, at least 90%, or at least 95% identical to any one of SEQ ID NOs 7-11, or that is any one of SEQ ID NOS 7-11 or a conservatively substituted variant thereof.

In some embodiments, the polypeptide is selected from the group consisting of:

(i) a polypeptide comprising an amino acid sequence which is at least 80%, preferably at least 85%, more preferably at least 90%, yet more preferably at least 95%, yet even more preferably at least 98%, particularly preferably at least 99%, or even 100% identical to, or which is, SEQ ID NO: 7;

(ii) a polypeptide comprising an amino acid sequence which is at least 80%, preferably at least 85%, more preferably at least 90%, yet more preferably at least 95%, yet even more preferably at least 98%, particularly preferably at least 99%, or even 100% identical to, or which is, SEQ ID NO: 8;

(iii) a polypeptide comprising an amino acid sequence which is at least 80%, preferably at least 85%, more preferably at least 90%, yet more preferably at least 95%, yet even more preferably at least 98%, particularly preferably at least 99%, or even 100% identical to, or which is, SEQ ID NO: 9;

(iv) a polypeptide comprising an amino acid sequence which is at least 80%, preferably at least 85%, more preferably at least 90%, yet more preferably at least 95%, yet even more preferably at least 98%, particularly preferably at least 99%, or even 100% identical to, or which is, SEQ ID NO: 10; and (v) a polypeptide comprising an amino acid sequence which is at least 80%, preferably at least 85%, more preferably at least 90%, yet more preferably at least 95%, yet even more preferably at least 98%, particularly preferably at least 99%, or even 100% identical to, or which is, SEQ ID NO: 11.

In some embodiments, the antibody is a polyclonal antibody. In some embodiments, the antibody is a monoclonal antibody.

The antibodies disclosed herein may be prepared by genetic immunization methods in which native proteins are expressed in vivo with normal post-transcriptional modifications, avoiding antigen isolation or synthesis. For example, hydrodynamic tail or limb vein delivery of naked plasmid DNA expression vectors can be used to produce the antigen of interest in vivo in mice, rats, and rabbits and thereby induce antigen-specific antibodies (Tang et al, Nature 356(6365): 152-4 (1992); Tighe et al, Immunol. Today 19(2) 89-97 (1998); Bates et al, Biotechniques, 40(2) 199-208 (2006)). This allows the efficient generation of high-titre, antigen-specific antibodies. Antibodies can also be derived by in vitro methods. Suitable examples include but are not limited to hybridoma technologies, phage display, yeast display and the like.

Kits

Another aspect of the invention provides a kit for detecting a virus in a biological sample from fish, wherein the kit comprises an oligonucleotide primer disclosed herein and/or an antibody disclosed herein.

In some embodiments, the kit is a real-time RT-PCR assay, for example the kit is a real-time RT-qPCR assay.

In some embodiments, the kit is for detecting a Totivirus in a biological sample from fish. In preferred embodiments, the kit is for detecting a Totivirus in a biological sample from lumpsucker fish.

Medical Uses and Vaccines

Another aspect of the invention provides an antibody for use in treating fish, particularly lumpsucker fish, against disease caused by Totivirus infection. In a preferred embodiment, the antibody is for use in treating fish, particularly lumpsucker fish, against disease caused by the virus disclosed herein (CLuTV). The antibody binds a polypeptide which is encoded by a nucleic acid sequence comprised within the genome of the virus disclosed herein.

In preferred embodiments, the fish is a lumpsucker fish.

In some embodiments, the fish show the following symptoms:

(i) tissue damage in the intestine, and/or (ii) diarrhoea; or (iii) cardiomyopathy.

The symptoms can be determined as described above. In preferred embodiments, the fish show symptoms of cardiomyopathy.

Another aspect of the invention provides a use of virus disclosed herein for producing a vaccine against disease caused by said virus.

Another aspect of the invention provides a vaccine comprising:

(i) a nucleic acid sequence which is comprised within the genome of the virus disclosed herein;

(ii) a nucleic acid sequence disclosed herein;

(iii) a viral polypeptide encoded by a nucleic acid sequence which is comprised within the genome of the virus disclosed herein;

(iv) a viral polypeptide comprising an amino acid sequence that is at least 80%, at least 90%, or at least 95% identical to any one of SEQ ID NOs 7-11, or that is any one of SEQ ID NOs 7-11 or a conservatively substituted variant thereof; or (v) a virus disclosed herein.

In certain embodiments, the vaccine contains several viral polypeptides, e.g., a first polypeptide that comprises an amino acid sequence that is at least 80% identical to SEQ ID NO: 7 and a second polypeptide that comprises an amino acid sequence that is at least 80% identical to SEQ ID NO: 8. The vaccine may contain one, two, three, four, or five viral polypeptides.

The vaccine is for protecting fish, particularly lumpsucker fish, against disease caused by Totivirus infection. In a preferred embodiment, the vaccine is for protecting fish, particularly lumpsucker fish, against disease caused by infection with the virus disclosed herein (CLuTV).

In some embodiments where the vaccine comprises a nucleic acid sequence comprised within the genome of the virus disclosed herein, said nucleic acid sequence comprises at least one of ORF-1, ORF-2, ORF-X, ORF-Y or ORF-Z, according to any of their embodiments disclosed herein. In preferred embodiments where the vaccine comprises a nucleic acid sequence comprised within the genome of the virus disclosed herein, said nucleic acid sequence comprises at least ORF-1 and ORF-2, according to any of their embodiments disclosed herein. In some embodiments where the vaccine comprises a nucleic acid sequence comprised within the genome of the virus disclosed herein, said nucleic acid sequence is, or is complementary to, a nucleic acid sequence which is at least 80%, preferably at least 85%, more preferably at least 90%, yet more preferably at least 95%, even more preferably at least 98%, particularly preferably at least 99%, or even 100% identical to, the sequence of the virus genome according to SEQ ID NO:6 (CLuTV).

The nucleic acid may be DNA or RNA.

In some embodiments where the vaccine comprises a viral polypeptide encoded by a nucleic acid sequence which is comprised within the genome of the virus disclosed herein, said polypeptide is selected from the group consisting of:

(i) a polypeptide comprising an amino acid sequence which is at least 80%, preferably at least 85%, more preferably at least 90%, yet more preferably at least 95%, yet even more preferably at least 98%, particularly preferably at least 99%, or even 100% identical to, or which is, SEQ ID NO: 7;

(ii) a polypeptide comprising an amino acid sequence which is at least 80%, preferably at least 85%, more preferably at least 90%, yet more preferably at least 95%, yet even more preferably at least 98%, particularly preferably at least 99%, or even 100% identical to, or which is, SEQ ID NO: 8;

(iii) a polypeptide comprising an amino acid sequence which is at least 80%, preferably at least 85%, more preferably at least 90%, yet more preferably at least 95%, yet even more preferably at least 98%, particularly preferably at least 99%, or even 100% identical to, or which is, SEQ ID NO: 9;

(iv) a polypeptide comprising an amino acid sequence which is at least 80%, preferably at least 85%, more preferably at least 90%, yet more preferably at least 95%, yet even more preferably at least 98%, particularly preferably at least 99%, or even 100% identical to, or which is, SEQ ID NO: 10; and (v) a polypeptide comprising an amino acid sequence which is at least 80%, preferably at least 85%, more preferably at least 90%, yet more preferably at least 95%, yet even more preferably at least 98%, particularly preferably at least 99%, or even 100% identical to, or which is, SEQ ID NO: 11.

In some embodiments where the vaccine comprises a virus disclosed herein, the genome of said virus comprises a nucleic acid sequence which is an RNA nucleic acid sequence comprising at least one of ORF-1, ORF-2, ORF-X, ORF-Y or ORF-Z, according to any of their embodiments disclosed herein. In some embodiments where the vaccine comprises a virus disclosed herein, the genome of said virus comprises a nucleic acid sequence which is an RNA nucleic acid sequence which is, or which is complementary to, a nucleic acid sequence which is at least 80%, preferably at least 85%, more preferably at least 90%, even more preferably at least 95%, yet even more preferably 98%, particularly preferably 99%, or even 100% identical to the sequence of the virus genome according to SEQ ID NO:6 (CLuTV).

In some embodiments, the vaccine comprises an amount of antigen which is in the range of 0.05 to 1.0 mg/ml, such as from 0.1 to 0.5 mg/ml, from 0.15 to 0.4 mg/ml, or from 0.2 to 0.3 mg/ml. The vaccine may be for administration in dosages of 0.005 to 0.5 mg/individual, preferably from 0.01 to 0.05 mg/individual, more preferably from 0.01 to 0.02 mg/individual.

In some embodiments, the vaccine comprises an amount of antigen corresponding to a $TCID_{50}$ of $10^5$ to $10^{10}$ per dosage, preferably a $TCID_{50}$ of $10^6$ to $10^9$ per dosage.

The vaccine may be in the form of a suspension of the virus or it may be lyophilized. In a lyophilized vaccine it may be useful to add one or more stabilizers. Suitable stabilizers are for example carbohydrates such as sorbitol, mannitol, starch, sucrose, dextran; protein containing agents such as bovine serum or skimmed milk; and buffers such as alkali metal phosphates.

The vaccine according to the invention may further be in a formulation comprising an adjuvant. Examples of adjuvants frequently used in fish and shellfish farming are muramyldipeptides, lipopolysaccharides, several glucans and glycans, mineral oil, Montanide™ and Carbopol®. An overview of adjuvants suitable for fish vaccines is given in the review paper of Sommerset (Expert Rev. Vaccines 4(1), 89-101 (2005)).

The vaccine of the invention may further comprise a suitable pharmaceutical carrier. In some embodiments the vaccine is formulated as an emulsion of water in oil. The vaccine may also comprise a so-called "vehicle". A vehicle is a device to which the antigen adheres, without being covalently bound to it. Such vehicles are inter alia biodegradable nano/micro-particles or -capsules of PLGA (polylactide-co-glycolic acid), alginate or chitosan, liposomes, niosomes, micelles, multiple emulsions and macrosols, all known in the art. A special form of such a vehicle, in which the antigen is partially embedded in the vehicle, is the so-called ISCOM.

In addition, the vaccine may comprise one or more suitable surface-active compounds or emulsifiers, e.g., Cremophore®, Tween® and Span®. Also, adjuvants such as interleukin, CpG and glycoproteins may be used.

In some embodiments, the vaccine is provided in fish feed, said feed may for example be pelleted or extruded feed.

Another aspect of the invention provides an interfering RNA (IRNA) molecule for use in treating fish, particularly lumpsucker fish, against disease caused by Totivirus infection. In a preferred embodiment, the iRNA is for use in treating fish, particularly lumpsucker fish, against disease caused by the virus disclosed herein (CLuTV). In a particular embodiment, the iRNA molecule comprises at least 12 (preferably contiguous) nucleotides of, or complementary to, a nucleic acid sequence comprised within the genome of the virus disclosed herein.

In preferred embodiments, the fish is a lumpsucker fish.

In some embodiments, the fish show the following symptoms:

(i) tissue damage in the intestine, and/or (ii) diarrhoea; or (iii) cardiomyopathy.

The symptoms can be determined as described above. In preferred embodiments, the fish show symptoms of cardiomyopathy.

In some embodiments, the iRNA molecule comprises at least 12 (preferably contiguous) nucleotides of, or complimentary to, a nucleic acid sequence comprising ORF-1, ORF-2, ORF-X, ORF-Y or ORF-Z, according to any of their embodiments disclosed herein. In some embodiments, the iRNA molecule comprises at least 12 (preferably contiguous) nucleotides of, or complimentary to, a nucleic acid sequence which is at least 80%, preferably at least 85%, more preferably at least 90%, even more preferably at least 95%, yet even more preferably 98%, particularly preferably 99%, or even 100% identical to the sequence of the virus genome according to SEQ ID NO:6 (CLuTV).

Sequences

The sequences referred to in the present disclosure are the following (see also the Figures and the sequence listing):

TABLE 1

| Sequence | Description |
|---|---|
| SEQ ID NO: 1 | CLuTV_ORF-1 nucleotide sequence |
| SEQ ID NO: 2 | CLuTV_ORF-2 nucleotide sequence |
| SEQ ID NO: 3 | CLuTV_ORF-X nucleotide sequence |
| SEQ ID NO: 4 | CLuTV_ORF-Y nucleotide sequence |
| SEQ ID NO: 5 | CLuTV_ORF-Z nucleotide sequence |
| SEQ ID NO: 6 | CLuTV_Genome nucleotide sequence |
| SEQ ID NO: 7 | CLuTV_ORF-1 amino acid sequence |
| SEQ ID NO: 8 | CLuTV_ORF-2 amino acid sequence |
| SEQ ID NO: 9 | CLuTV_ORF-X amino acid sequence |
| SEQ ID NO: 10 | CLuTV_ORF-Y amino acid sequence |
| SEQ ID NO: 11 | CLuTV_ORF-Z amino acid sequence |
| SEQ ID NO: 12 | CLP01 Forward primer |
| SEQ ID NO: 13 | CLP01 Taqman Probe |
| SEQ ID NO: 14 | CLP01 Reverse primer |
| SEQ ID NO: 15 | CLP02 Forward primer |
| SEQ ID NO: 16 | CLP02 Taqman Probe |
| SEQ ID NO: 17 | CLP02 Reverse primer |
| SEQ ID NO: 18 | CLP03 Forward primer |
| SEQ ID NO: 19 | CLP03 Taqman Probe |
| SEQ ID NO: 20 | CLP03 Reverse primer |

Other suitable oligonucleotide primers referred to herein are provided in Table 2:

| SEQ ID NO | Primer name | primer sequence |
|---|---|---|
| 21 | PCL_F1 | ATGGACGCAAACAAAGAAACA |
| 22 | PCL_R1 | CCAATGCTGTTCATGAAACC |
| 23 | PCL_F2 | CCGGACCTCTTTCAAGTAGTG |
| 24 | PCL_R2 | GCATCTCACTCACGATGGCT |
| 25 | PCL_F3 | TGGGAACACACAGGACTGGG |
| 26 | PCL_R3 | CTCCATGCAATCTGACCTTG |
| 27 | PCL_F4 | ACTTGTGCTGGTGAGCTAGTGA |
| 28 | PCL_R4 | ATCCAGGACGGTGGCGT |
| 29 | PCL_F5 | TTAGAGAAACAAACTTGACCCATC |
| 30 | PCL_R5 | CGACGAGTATGTCAACTAGCATATT |
| 31 | PCL_F6 | CAAATGACAGACGACGTCAGG |
| 32 | PCL_R6 | CCAGTGCTGAAGGTGTTTGA |
| 33 | PCL_F7 | CCGATATTGCGGGTTTAACCCA |
| 34 | PCL_R7 | CGCTACGAAAGCTGAGACCG |
| 35 | PCL_F8 | GTTGTTACAGTGTAAGTGCTGTGTT |
| 36 | PCL_R8 | TTACCGAGAGTGAGTAGAAACTGAA |
| 37 | PCL_F9 | ACGCCACCGTCCTGGAT |
| 38 | PCL_R9 | CCTGACGTCGTCTGTCATTTG |
| 39 | PCL_F10 | CGGTCTCAGCTTTCGTAGCG |
| 40 | PCL_R10 | AACACAGCACTTACACTGTAACAAC |

Further oligonucleotide primers referred to herein are provided in Table 3:

| SEQ ID NO | primer sequence |
|---|---|
| 41 | CCTACACTTACAGCCACAGAGTGCC |
| 42 | TGGTGGCGGCGCTAGCTGTCAGGAGAGGAAAGAGAAG |
| 43 | ACTCAACATAAAGTTATACTCATGGCTAAAATTTATT ACACTACAGGAACAGCAGGAAAACGATGGGTGTAGGT GAAGGCTAGAGAAGCCAAATACAGGTTTTCTTATCTT CCTTTTGTGGG |
| 44 | TGCAGGTATTTCCTCACCCGTCAGC |
| 45 | AGTACATCATACAATACATGATCAACTGCTCTGATTA CATTATTAATTGAAATT |
| 46 | CAGGTTCACAATGACCACCTCAT |
| 47 | CGATGTGGGATAACGAACCGGGTAA |

-continued

| SEQ ID NO | primer sequence |
|-----------|-----------------|
| 48 | TTACAGGGTTCCTGCCTAAATGAATCATCATCCAAGG ATTTACAAAAAATTATAGCCTTGKCACCCCAACCATT ATAGCTATCATAACCCTACTCAACCTGTACTCTTACA TACACCTCAT |
| 49 | TATCACATCCACTTGATCCAAAGCTGAGTTGAGGTTC TGAATACCTTTGTTAATTTTCTGTCTCAATGACCTAA TATTGTCAGTGGAGTGTTAAATC |

EXAMPLES

The following examples illustrate the present invention. They are intended to aid in the understanding of the invention, and they should not be construed to in any way limit the scope of the invention.

Example 1: Identification of CLuTV

Fish samples were obtained from a lumpsucker (*Cyclopterus lumpus*) farming site experiencing high mortality (60-80%). The samples were analyzed using standard real-time RT-PCR and histology. No known pathogens were identified using real-time RT-PCR. Histological analysis indicated signs of tissue damage in the intestine in the affected individuals, but no potentially pathogenic bacteria and no microparasites could be observed.

Total RNA was extracted from moribund fish in a phenol/chloroform extraction protocol (Qiagen RNeasy® 96 Universal Tissue Kit), and this RNA was used as a template in a Next Generation Sequencing (NGS) analysis. The NGS analysis was performed by the company BaseClear (https://www.baseclear.com/), and yielded approximately 98 million sequence reads, where the majority came from the host transcriptome. Approximately 28,600 of the assembled reads from the NGS analysis were found to have no significant nucleotide match in the National Center for Biotechnology Information (NCBI) GenBank. From these reads, a novel virus sequence-herein termed *Cyclopterus lumpus Totivirus or CLuTV*—was identified and characterized by the inventors. The DNA sequences obtained from the NGS analysis are provided in FIGS. 2 to 5 (see also SEQ ID Nos: 1 to 6). However, it will be appreciated that the corresponding RNA sequences are present in the virus CLuTV.

The sequence of CLuTV was identified herein to be 6,353 nucleotides long, and it contains five possible open reading frames (ORFs). A schematic is shown in FIG. 1. A relationship between CLuTV and other known viruses could only be determined by comparison of translated amino acid sequences. The length and organization of the genome, together with downstream sequence analyses, indicate that it is a novel virus in the Totiviridae family, with the Atlantic salmon virus, PMCV as its closest relative. Preliminary results indicate that, at least in Norway, CLuTV has a significant presence in farmed lumpsucker.

Figure 9:
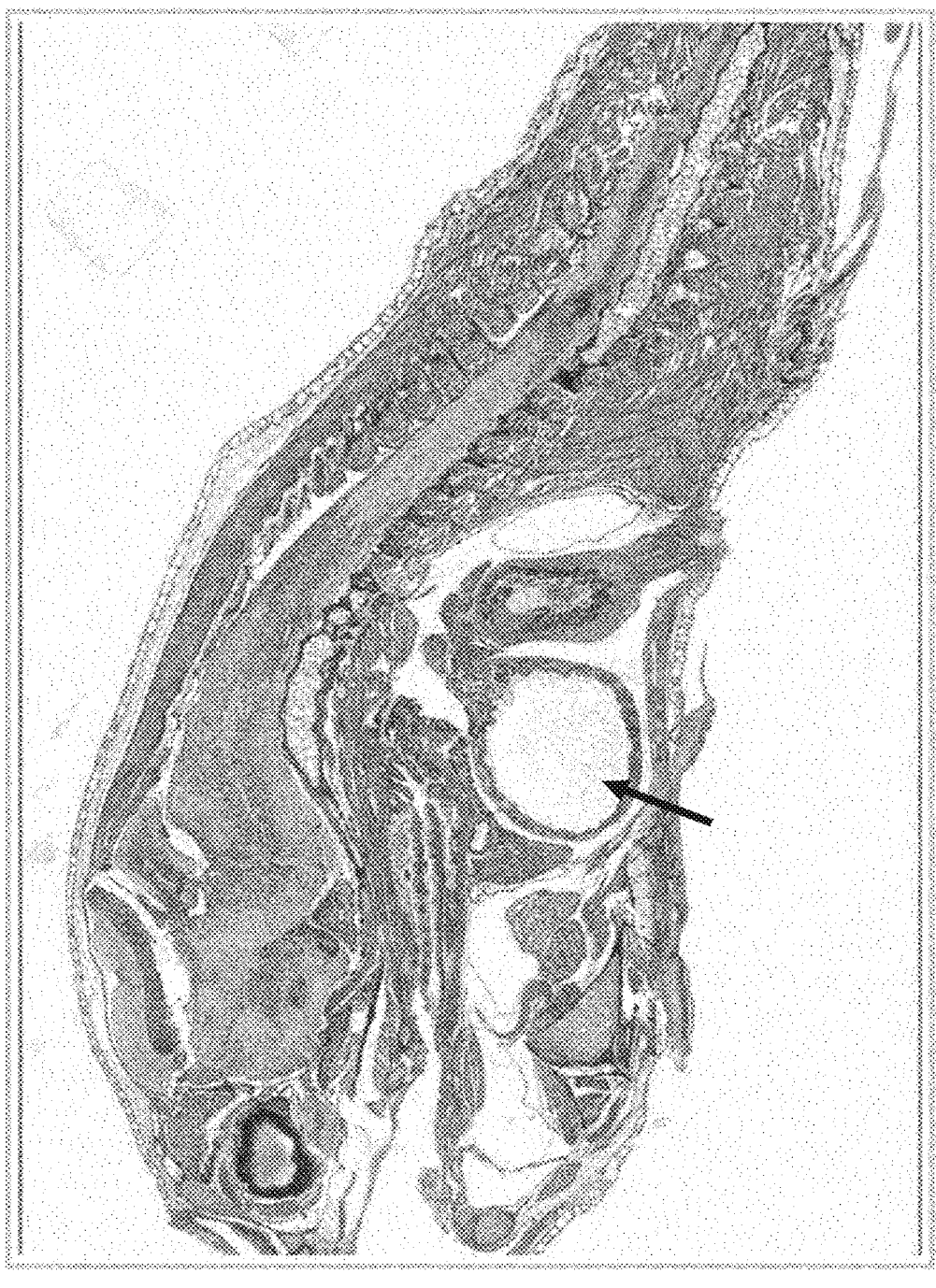
FIG. 9: Haematoxylin and Eosin stain of a whole section of affected lumpsucker, showing accumulation of fluid in the stomach (arrow).
Figure 10:
FIG. 10: Haematoxylin and Eosin stain of a section of lumpsucker intestine showing accumulation of mucus, and cellular discharge (arrows).
Figure 11:
FIG. 11: Haematoxylin and Eosin stain of a section of lumpsucker intestine showing accumulation of mucus (arrow), and cellular discharge.
Figure 12:
FIG. 12: Haematoxylin and Eosin stain of a section of lumpsucker intestine showing accumulation of mucus (arrow).

The pathology associated with CLuTV in lumpsucker is shown by FIGS. 9 to 12. Lumpsucker sections were stained using a Haematoxylin and Eosin (H&E) histological stain. FIG. 9 is a whole section of affected lumpsucker, showing accumulation of fluid in the stomach (arrow). FIG. 10 is a section of lumpsucker intestine showing accumulation of mucus, and cellular discharge (arrows). FIG. 11 is a section of lumpsucker intestine showing accumulation of mucus (arrow), and cellular discharge. FIG. 12 is a section of lumpsucker intestine showing accumulation of mucus (arrow).

Example 2: Nucleotide Sequence Analysis of CLuTV

The nucleotide sequence of CLuTV from the NGS analysis was confirmed by conventional Sanger sequencing of RT-PCR products derived from total RNA extracted from moribund fish.

When performing a standard nucleotide BLAST search using the CLuTV sequence, no match was found in the NCBI GeneBank. If parameters of the search were altered to include more dissimilar sequences in the search, some sequence regions from other known viruses were identified. The percentage of nucleotide sequence identity ("Seq. Id.") between these CLuTV regions and regions from other known viruses is shown in Table 2.

TABLE 2

| Best nucleotide match found between CLuTV and known viruses in the NCBI GeneBank | | | | | | | |
|---|---|---|---|---|---|---|---|
| CL_VirusA | | Best sequence region match (NCBI GeneBank) | | | | | |
| Region | | | | | Seq. | | |
| Start | Stop | Start | Stop | bp | Id. (%) | Acc. No. | Description |
| 3535 | 3596 | 145 | 207 | 63 | 83% | JQ745678 | PMCV, AL V-708, Isolate 1198 |
| 3534 | 3596 | 3723 | 3785 | 63 | 81% | HQ339954 | PMCV, AL V-708, RdRp gene |
| 3132 | 3248 | 3321 | 3437 | 118 | 71% | HQ339954 | PMCV, AL V-708, complete genome |
| 3534 | 3596 | 145 | 207 | 63 | 79% | JQ745677 | PMCV, AL V-708, isolate 708 |

PMCV, the closest relative to CLuTV, contains three ORFs in its genome. ORF3 from PMCV resides in the same region as ORFX-Y in CLuTV.

Example 3: Amino Acid Sequence Analysis of CLuTV

Translation of the ORFs of CLuTV yields a total of five potential proteins. The amino acid identity between the CLuTV ORFs and other known proteins from other viruses is shown in Table 3. Only the best match for each ORF is provided.

TABLE 3

Best amino acid sequence match found between CLuTV and known viruses in the NCBI GeneBank

| CL_ | | | | | | Best aa sequence match (NCBI GeneBank) | |
| --- | --- | --- | --- | --- | --- | --- | --- |
| VirusA ORF | Amino acids | Total Score | Query cover. | E-value | Identity (%) | Accession number | Description |
| ORF01 | 828 | 421 | 96% | 2.00E−131 | 33% | YP009229914 | structural protein [ PMCV] |
| ORF02 | 647 | 451 | 99% | 2.00E−146 | 40% | YP004581250 | ORF2 [ PMCV AL V-708] |
| ORFX | 90 | 41.2 | 67% | 0.022 | 40% | AKH03114 | p10 [Avian orthoreovirus) |
| ORFY | 118 | NA | NA | NA | NA | NA | No Match |
| ORFY | 112 | NA | NA | NA | NA | NA | No Match |

Example 4: Evaluating the Presence of CLuTV in Farmed Lumpfish Populations

Three separate real-time RT-PCR assays (CLP01, CLP02 and CLP03) were designed using the primers according to SEQ ID NOs: 12 to 14, 15 to 17 and 18 to 20, respectively. CLP01 targeted ORF-1, CLP02 targeted ORF-2, and CLP03 targeted ORF-Y. The original fish sample material was confirmed to be positive for CLUTV using all three of these assays.

For more extensive investigation, assay CLP01 was selected to evaluate the presence of CLuTV in existing farmed lumpfish populations. The results from screening different lumpfish populations in Norway are shown in Table 4.

TABLE 4

Results from testing of NGS material and field material
Screening of lumpfish populations (Norway)

| County | Samples (N) | Positive (N) | Prevalence (%) |
| --- | --- | --- | --- |
| Finnmark | 60 | 59 | 98.3 |
| Troms | 28 | 3 | 10.7 |
| Møre | 67 | 0 | 0.0 |
| Trøndelag | 64 | 35 | 54.7 |
| Rogaland | 20 | 18 | 90.0 |
| Vest-Agder | 60 | 3 | 5.0 |

As the table shows, certain lumpfish populations, in particular those from the Finnmark and Rogaland counties, have a CLuTV prevalence of over 90%.

In view of the disclosure provided herein, it will be appreciated that the present invention also encompasses the following items:

1. A nucleic acid, wherein the sequence of said nucleic acid comprises
(a) at least one open reading frame (ORF) sequence selected from the group consisting of ORF-1, ORF-2, ORF-X, ORF-Y and ORF-Z, or
(b) a sequence complementary thereto;
wherein
ORF-1 is at least 80% identical to the nucleic acid sequence of SEQ ID NO:1,
ORF-2 is at least 80% identical to the nucleic acid sequence of SEQ ID NO:2,
ORF-X is at least 80% identical to the nucleic acid sequence of SEQ ID NO:3,
ORF-Y is at least 80% identical to the nucleic acid sequence of SEQ ID NO:4, and
ORF-Z is at least 80% identical to the nucleic acid sequence of SEQ ID NO:5.

2. The nucleic acid of item 1, wherein
ORF-1 is at least 85% identical to the nucleic acid sequence of SEQ ID NO:1,
ORF-2 is at least 85% identical to the nucleic acid sequence of SEQ ID NO:2,
ORF-X is at least 85% identical to the nucleic acid sequence of SEQ ID NO:3,
ORF-Y is at least 85% identical to the nucleic acid sequence of SEQ ID NO:4, and
ORF-Z is at least 85% identical to the nucleic acid sequence of SEQ ID NO:5.

3. The nucleic acid of item 1 or 2, wherein
ORF-1 is at least 90% identical to the nucleic acid sequence of SEQ ID NO:1,
ORF-2 is at least 90% identical to the nucleic acid sequence of SEQ ID NO:2,
ORF-X is at least 90% identical to the nucleic acid sequence of SEQ ID NO:3,
ORF-Y is at least 90% identical to the nucleic acid sequence of SEQ ID NO:4, and
ORF-Z is at least 90% identical to the nucleic acid sequence of SEQ ID NO:5.

4. The nucleic acid of any one of items 1-3, wherein
ORF-1 is at least 95% identical to the nucleic acid sequence of SEQ ID NO:1,
ORF-2 is at least 95% identical to the nucleic acid sequence of SEQ ID NO:2,
ORF-X is at least 95% identical to the nucleic acid sequence of SEQ ID NO:3,
ORF-Y is at least 95% identical to the nucleic acid sequence of SEQ ID NO:4, and
ORF-Z is at least 95% identical to the nucleic acid sequence of SEQ ID NO:5.

5. The nucleic acid of any one of items 1-4, wherein
ORF-1 is at least 98% identical to the nucleic acid sequence of SEQ ID NO:1,
ORF-2 is at least 98% identical to the nucleic acid sequence of SEQ ID NO:2,
ORF-X is at least 98% identical to the nucleic acid sequence of SEQ ID NO:3,
ORF-Y is at least 98% identical to the nucleic acid sequence of SEQ ID NO:4, and
ORF-Z is at least 98% identical to the nucleic acid sequence of SEQ ID NO:5.

6. The nucleic acid of any one of items 1-5, wherein
ORF-1 is at least 99% identical to the nucleic acid sequence of SEQ ID NO:1,
ORF-2 is at least 99% identical to the nucleic acid sequence of SEQ ID NO:2,
ORF-X is at least 99% identical to the nucleic acid sequence of SEQ ID NO:3,
ORF-Y is at least 99% identical to the nucleic acid sequence of SEQ ID NO:4, and ORF-Z is at least 99% identical to the nucleic acid
sequence of SEQ ID NO:5.

7. The nucleic acid of any one of items 1-6, wherein

ORF-1 is 100% identical to the nucleic acid sequence
of SEQ ID NO:1,

ORF-2 is 100% identical to the nucleic acid sequence
of SEQ ID NO:2,

ORF-X is 100% identical to the nucleic acid sequence
of SEQ ID NO:3,

ORF-Y is 100% identical to the nucleic acid sequence
of SEQ ID NO:4, and

ORF-Z is 100% identical to the nucleic acid sequence
of SEQ ID NO:5.

8. A nucleic acid, wherein the sequence of said nucleic
acid is at least 80% identical to a corresponding
sequence present within SEQ ID NO:6, preferably at
least 85% identical, more preferably at least 90%
identical, yet more preferably at least 95% identical, yet
more preferably at least 98% identical, yet even more
preferably at least 99% identical, and particularly pref-
erably 100% identical.

9. A nucleic acid, wherein the sequence of said nucleic
acid is at least 80% identical to a corresponding
sequence present within a sequence that is complemen-
tary to SEQ ID NO:6, preferably at least 85% identical,
more preferably at least 90% identical, yet more pref-
erably at least 95% identical, yet more preferably at
least 98% identical, yet even more preferably at least
99% identical, and particularly preferably 100% iden-
tical.

10. The nucleic acid of items 8 or 9, wherein the sequence
of said nucleic acid comprises 200 nucleotides or less.

11. The nucleic acid of any one of items 8 to 10, wherein
the sequence of said nucleic acid comprises at least 60
nucleotides.

12. The nucleic acid of item 11, wherein the sequence of
said nucleic acid comprises at least 100 nucleotides,
preferably at least 150 nucleotides.

13. The nucleic acid of item 8 or 9, wherein the sequence
of said nucleic acid comprises at least 200 nucleotides.

14. Use of the nucleic acid of any one of items 1-13
(a) as a hybridization probe;
(b) for detecting the virus disclosed herein in a bio-
logical sample of a fish, particularly lumpfish;
(c) in a method for detecting a virus that infects and is
capable of killing fish, particularly lumpfish;
(d) in a method for detecting a virus that infects and is
capable of killing fish, particularly lumpfish, accord-
ing to any of the corresponding methods disclosed
herein;
(e) for preparing a vaccine for protecting fish, particu-
larly lumpsucker fish, against disease caused by
Totivirus, infection; or
(f) for preparing a vaccine for protecting fish, particu-
larly lumpsucker fish, against disease caused by a
virus disclosed herein, such as the virus of items
18-25 below.

15. The nucleic acid of item 1, wherein the sequence of
said nucleic acid comprises at least ORF-1 and ORF-2,
as defined in any of items 1 to 7, or a sequence that is
complementary thereto.

16. The nucleic acid of item 1, wherein the sequence of
said nucleic acid is at least 80% identical to the virus
genome according to SEQ ID NO:6, preferably at least
85% identical, more preferably at least 90% identical,
yet more preferably at least 95% identical, yet more preferably at least 98% identical, yet even more pref-
erably at least 99% identical, and particularly prefer-
ably 100% identical.

17. The nucleic acid of item 1, wherein the sequence of
said nucleic acid is at least 80% identical a sequence
that is complementary to SEQ ID NO:6, preferably at
least 85% identical, more preferably at least 90%
identical, yet more preferably at least 95% identical, yet
more preferably at least 98% identical, yet even more
preferably at least 99% identical, and particularly pref-
erably 100% identical.

18. A virus, in particular a virus that infects and is capable
of killing lumpsucker fish (such as *Cyclopterus lum-
pus*), wherein the virus genome comprises the nucleic
acid sequence of the nucleic acid of any one of items 1
to 13 and 15 to 17, wherein said nucleic acid sequence
comprised in the virus genome contains the base uracil
(U) instead of the base thymine (T).

19. The virus of item 18, wherein the infection of lump-
sucker fish by the virus causes the following symptoms
in the fish:
(i) tissue damage in the intestine, and/or
(ii) diarrhoea; or
(iii) cardiomyopathy.

20. A virus that comprises one or more, preferably two or
more, more preferably three or more, more preferably
four or more, yet more preferably five of ORFs 1, 2, X,
Y, and Z, wherein said ORFs 1, 2, X, Y, Z encode viral
polypeptides of SEQ ID NOs 7-11, respectively, or
viral polypeptides that are at least 80% identical to SEQ
ID NOs 7-11, respectively.

21. The virus of item 20, wherein said ORFs 1, 2, X, Y,
and Z encode viral polypeptides of SEQ ID NOS 7-11,
respectively, or viral polypeptides that are at least 90%
identical to SEQ ID NOS 7-11, respectively.

22. The virus of item 20, wherein said ORFs 1, 2, X, Y,
and Z encode viral polypeptides of SEQ ID NOS 7-11,
respectively, or viral polypeptides that are at least 95%
identical to SEQ ID NOS 7-11, respectively.

23. The virus of any one of items 20-22, wherein said
ORFs 1, 2, X, Y, and Z encode viral polypeptides that
are conservatively substituted variants of SEQ ID NOs
7-11, respectively.

24. The virus of any one of items 18-23, wherein the virus
is a non-enveloped virus.

25. The virus of any one of items 18 to 24, wherein the
virus is a Totivirus.

26. An oligonucleotide primer which comprises a
sequence of at least 9 consecutive nucleotides, prefer-
ably of at least 12 consecutive nucleotides, more pref-
erably of at least 15 consecutive nucleotides, and
particularly preferably of at least 18 consecutive
nucleotides, wherein said sequence is comprised within
the genome of the virus of any one of items 18 to 25,
preferably with the proviso that said primer does not
comprise SEQ ID NOs 41-49.

27. An oligonucleotide primer which comprises a
sequence of at least 9 consecutive nucleotides, prefer-
ably of at least 12 consecutive nucleotides, more pref-
erably of at least 15 consecutive nucleotides, and
particularly preferably of at least 18 consecutive
nucleotides, wherein said sequence is complementary
to a nucleic acid sequence comprised within the
genome of the virus of any one of items 18 to 25,
preferably with the proviso that said primer does not
comprise SEQ ID NOs 41-49.

28. An oligonucleotide primer which comprises a sequence of at least 9 consecutive nucleotides, preferably of at least 12 consecutive nucleotides, more preferably of at least 15 consecutive nucleotides, and particularly preferably of at least 18 consecutive nucleotides, wherein said sequence is at least 80% identical to a sequence comprised within SEQ ID NO:6, preferably with the proviso that said primer does not comprise SEQ ID NOs 41-49.

29. An oligonucleotide primer which comprises a sequence of at least 9 consecutive nucleotides, preferably of at least 12 consecutive nucleotides, more preferably of at least 15 consecutive nucleotides, and particularly preferably of at least 18 consecutive nucleotides, wherein said sequence is at least 80% identical to a sequence comprised within a sequence complementary to SEQ ID NO:6, preferably with the proviso that said primer does not comprise SEQ ID NOs 41-49.

30. The oligonucleotide primer of item 28 or 29, wherein said percentage sequence identity is at least 85%, preferably at least 90%, more preferably at least 95%, yet more preferably at least 98%, yet even more preferably at least 99%, and particularly preferably 100%.

31. The oligonucleotide primer of any one of items 22 to 26, wherein said oligonucleotide primer is 9 to 60 nucleotides in length, preferably 12 to 40 nucleotides in length, more preferably 15 to 30 nucleotides in length, particularly preferably 18 to 25 nucleotides in length.

32. The oligonucleotide primer of any one of items 22 to 24, wherein said sequence comprised therein represents, or is complementary to, a portion of a reference nucleic acid sequence selected from the group consisting of SEQ ID NO:1, SEQ ID NO:2, SEQ ID NO:3, SEQ ID NO: 4, SEQ ID NO:5 or SEQ ID NO:6.

33. An oligonucleotide primer which comprises at least 9 consecutive nucleotides, preferably at least 12 consecutive nucleotides, more preferably at least 15 consecutive nucleotides, and particularly preferably at least 18 consecutive nucleotides, of a sequence which is at least 80% identical to a sequence which is, or which is complementary to, a sequence selected from the group consisting of SEQ ID NO: 12 to SEQ ID NO:40, preferably with the proviso that said primer does not comprise SEQ ID NOs 41-49.

34. Use of at least one oligonucleotide primer in a method of detecting the virus of any one of items 18 to 25, wherein the at least one primer comprises a sequence of at least 9 consecutive nucleotides, preferably of at least 12 consecutive nucleotides, more preferably of at least 15 consecutive nucleotides, and particularly preferably of at least 18 consecutive nucleotides, and wherein said sequence is complementary to a nucleic acid sequence which is comprised within the genome of said virus, preferably with the proviso that said primer does not comprise SEQ ID NOs 41-49.

35. Use of at least one nucleic acid of any one of items 1 to 13 or 15 to 17, or of at least one oligonucleotide primer of any one of items 26 to 34 in a method of detecting a fish virus, optionally wherein the virus infects and is capable of killing lumpsucker fish.

36. The use of item 35, wherein said nucleic acid, or said oligonucleotide primer is used in a method of detecting the virus of any one of items 18 to 25.

37. A method for detecting a virus that infects and is capable of killing fish, in particular lumpsucker fish, comprising the steps of:

(a) contacting a nucleic acid extracted from a biological sample of a fish with at least one oligonucleotide primer to form a mixture, wherein the at least one oligonucleotide primer is complementary to a nucleic acid sequence which is comprised within the genome of the virus of any one of items 18 to 25, (b) determining whether upon subjecting the mixture of a) to amplification an amplification product is present, wherein the presence of amplification product indicates the presence of RNA associated with the virus, and hence the presence of the virus in the biological sample.

38. The method of item 37, wherein the oligonucleotide primer is an oligonucleotide primer of any one of items 26 to 34.

39. The method of items 37 or 38, wherein the nucleic acid in step (a) of the method, for example RNA, is extracted from biological samples by using solid-phase extraction, e.g., on-column purification using a solid phase of silica gel membrane.

40. The method of any one of items 37 to 38, wherein the nucleic acid in step (a) of the method, for example RNA, is extracted from biological samples by using phenol/chloroform extraction.

41. A method for detecting a virus that infects and is capable of killing fish, in particular lumpsucker fish, comprising the steps of:

(a) sequencing a nucleic acid extracted from a biological sample of a fish, and (b) comparing the resulting nucleic acid sequence with a nucleic acid sequence which is, or which is complementary to, a reference sequence selected from the group consisting of SEQ ID NO:1, SEQ ID NO:2, SEQ ID NO:3, SEQ ID NO:4, SEQ ID NO: 5 and SEQ ID NO:6, wherein an at least 80% sequence identity between the two sequences indicates the presence of the virus in the biological sample.

42. The method of item 41, wherein the percentage sequence identity between the two sequences that indicates the presence of the virus in the biological sample is at least 85%, preferably at least 90%, more preferably at least 95%, yet more preferably at least 98%, yet even more preferably at least 99%, and particularly preferably 100%.

43. A viral polypeptide comprising an amino acid sequence that is at least 80% identical to any one of SEQ ID NOS 7-11.

44. The viral polypeptide according to item 43, comprising an amino acid sequence that is at least 90% identical to any one of SEQ ID NOs 7-11.

45. The viral polypeptide according to item 43 or 44, comprising an amino acid sequence that is at least 95% identical to any one of SEQ ID NOS 7-11.

46. The viral polypeptide according to any one of items 43-45, comprising an amino acid sequence comprising any one of SEQ ID NO: 7-11 or a conservatively substituted variant thereof.

47. The viral polypeptide according to any one of items 43-45, comprising an amino acid sequence comprising SEQ ID NOS 7-11.

48. An antibody that binds a polypeptide, wherein the polypeptide is encoded by a nucleic acid sequence which is comprised within the genome of the virus of any one of items 18 to 25, or is a viral polypeptide encoded by a nucleic acid of any one of items 1-13 and 15-17.

49. An antibody that binds a polypeptide selected from the group consisting of:

(i) a polypeptide comprising an amino acid sequence which is at least 80%, preferably at least 85%, more preferably at least 90%, yet more preferably at least 95%, yet even more preferably at least 98%, particularly preferably at least 99%, or even 100% identical to, SEQ ID NO:7;

(ii) a polypeptide comprising an amino acid sequence which is at least 80%, preferably at least 85%, more preferably at least 90%, yet more preferably at least 95%, yet even more preferably at least 98%, particularly preferably at least 99%, or even 100% identical to, SEQ ID NO:8;

(iii) a polypeptide comprising an amino acid sequence which is at least 80%, preferably at least 85%, more preferably at least 90%, yet more preferably at least 95%, yet even more preferably at least 98%, particularly preferably at least 99%, or even 100% identical to, SEQ ID NO:9;

(iv) a polypeptide comprising an amino acid sequence which is at least 80%, preferably at least 85%, more preferably at least 90%, yet more preferably at least 95%, yet even more preferably at least 98%, particularly preferably at least 99%, or even 100% identical to, SEQ ID NO: 10; and (v) a polypeptide comprising an amino acid sequence which is at least 80%, preferably at least 85%, more preferably at least 90%, yet more preferably at least 95%, yet even more preferably at least 98%, particularly preferably at least 99%, or even 100% identical to, SEQ ID NO:11.

50. A kit for detecting a virus in a biological sample from fish, wherein the kit comprises a nucleic acid of any one of items 1-13 or 15 to 17, an oligonucleotide primer of any one of items 26 to 34 and/or an antibody of item 48 or item 49.

51. The kit of item 50, wherein the kit is suitable to conduct, or is for use for conducting, a real-time RT-PCR assay.

52. The antibody of item 48 or item 49 for use in treating fish infected with a virus, in particular lumpsucker fish.

53. The antibody of item 52, wherein the virus is the virus of any one of items 18 to 25.

54. Use of the virus of any one of items 18 to 21 for producing a vaccine.

55. A vaccine comprising:

(i) a nucleic acid sequence which is comprised within the genome of the virus of any one of items 18 to 25;

(ii) a nucleic acid sequence of any one of items 1 to 13 or 15 to 17;

(iii) a viral polypeptide encoded by a nucleic acid sequence comprised within the genome of the virus of any one of items 18 to 25;

(iv) a viral polypeptide encoded by a nucleic acid sequence of any one of items 1 to 13 or 15 to 17;

(v) a viral polypeptide according to any one of items 43-47, or (vi) a virus of any one of items 18 to 25.

56. The vaccine of item 55, wherein the sequence of the nucleic acid is the sequence of the nucleic acid referred to in any one of items 1 to 13 or 17, wherein said nucleic acid sequence contains the base uracil (U) instead of the base thymine (T).

57. An interfering RNA (iRNA) molecule for use in treating fish infected with a virus, particularly lumpsucker fish, wherein the iRNA molecule comprises at least 12 (preferably contiguous) nucleotides of, or complementary to, a nucleic acid sequence comprised within the genome of the virus of any one of items 18 to 25.

58. An interfering RNA (iRNA) molecule for use in treating fish infected with a virus, particularly lumpsucker fish, wherein the iRNA molecule comprises at least 12 (preferably contiguous) nucleotides of, or complimentary to, a nucleic acid sequence which is at least 80%, preferably at least 85%, more preferably at least 90%, even more preferably at least 95%, yet even more preferably 98%, particularly preferably 99%, or even 100% identical to the sequence of the virus genome according to SEQ ID NO:6 (CLuTV).

59. The interfering RNA of item 57 or item 58, wherein said iRNA molecule comprises at least 15 and more preferably at least 18 of said (preferably contiguous) nucleotides.

Those skilled in the art will recognize, or be able to ascertain using no more than routine experimentation and/or common general knowledge, numerous equivalents to the specific aspects, items and embodiments disclosed herein both in the Examples and in the body of the entire patent description. Such equivalents are considered to be within the scope of this invention and are intended to be encompassed by the following claims, or any claims that may be pursued based on the present disclosure.

The invention claimed is:

1. A nucleic acid, wherein the sequence of said nucleic acid comprises at least one open reading frame (ORF) sequence selected from the group consisting of ORF-1, ORF-2, ORF-X,
  ORF-Y and ORF-Z; wherein
  ORF-1 is at least 80% identical to the nucleic acid sequence of SEQ ID NO:1,
  ORF-2 is at least 80% identical to the nucleic acid sequence of SEQ ID NO:2,
  ORF-X is at least 80% identical to the nucleic acid sequence of SEQ ID NO:3,
  ORF-Y is at least 80% identical to the nucleic acid sequence of SEQ ID NO:4, and
  ORF-Z is at least 80% identical to the nucleic acid sequence of SEQ ID NO:5.

2. The nucleic acid of claim 1, wherein
  (a) the sequence of said nucleic acid comprises at least ORF-1 and ORF-2, as defined in claim 1; and/or
  (b) the sequence of said nucleic acid is at least 80% identical to the virus genome according to SEQ ID NO:6.

3. A nucleic acid, wherein
  (a) the sequence of said nucleic acid is complementary to SEQ ID NO: 1 and/or to SEQ ID NO: 2; and/or
  (b) the sequence of said nucleic acid is complementary to SEQ ID NO: 6.

4. A virus that infects and is capable of killing lumpsucker fish (*Cyclopterus lumpus*), wherein the virus genome comprises the sequence of a nucleic acid of claim 1, wherein said nucleic acid sequence contains the base uracil (U) instead of the base thymine (T).

5. The virus of claim 4, wherein said virus comprises ORF-1, ORF-2, ORF-X, ORF-Y and ORF-Z as defined in claim 1, and wherein said ORF-1, ORF-2, ORF-X, ORF-Y and ORF-Z encode viral polypeptides that are at least 80% identical to SEQ ID NOs 7-11, respectively.

6. The virus of claim 5, wherein said ORF-1, ORF-2, ORF-X, ORF-Y and ORF-Z encode viral polypeptides that are at least 95% identical to SEQ ID NOs 7-11, respectively.

7. The virus of claim 5, wherein said ORF-1, ORF-2, ORF-X, ORF-Y and ORF-Z encode viral polypeptides that are conservatively substituted variants of SEQ ID NOs 7-11, respectively, or viral polypeptides comprising the amino acid sequences of SEQ ID NOs 7-11, respectively.

8. The virus of claim 4, wherein the infection of lumpsucker fish by the virus causes the following symptoms in the fish:
  (i) tissue damage in the intestine, and/or
  (ii) diarrhoea; or
  (iii) cardiomyopathy.

9. The virus of claim 4, wherein
  (a) the virus is a non-enveloped virus; and/or
  (b) the virus is a Totivirus.

10. An oligonucleotide primer which
  (a) comprises at least 9 consecutive nucleotides, wherein the sequence is complementary to a nucleic acid sequence which is comprised within the genome of the virus of any one of claims 4 to 6;
  (b) comprises at least 9 consecutive nucleotides of a sequence which is, or which is complementary to, a portion of a reference nucleic acid sequence selected from the group consisting of SEQ ID NO:1, SEQ ID NO:2, SEQ ID NO:3, SEQ ID NO:4, SEQ ID NO: 5 or SEQ ID NO:6; or
  (c) comprises at least 9 consecutive nucleotides of a sequence which is at least 80% identical to a sequence which is, or which is complementary to, a sequence selected from the group consisting of SEQ ID NO: 12 to SEQ ID NO:40;
with the proviso that said oligonucleotide primer does not comprise a sequence selected from the group consisting of SEQ ID NO:41 to SEQ ID NO:49.

11. A method for detecting a virus that infects and is capable of killing fish, comprising the steps of:

(a) contacting a nucleic acid extracted from a biological sample of a fish with at least one oligonucleotide primer to form a mixture, wherein the at least one oligonucleotide primer is complementary to a nucleic acid sequence which is comprised within the genome of the virus of claim 4, and (b) determining whether upon subjecting the mixture of a) to amplification an amplification product is present, wherein the presence of amplification product indicates the presence of RNA associated with the virus, and hence the presence of the virus in the biological sample.

12. A method for detecting a virus that infects and is capable of killing fish, comprising the steps of:

(a) sequencing a nucleic acid extracted from a biological sample of a fish, and (b) comparing the resulting nucleic acid sequence with a nucleic acid sequence which is, or which is complementary to, a reference sequence selected from the group consisting of SEQ ID NO:1, SEQ ID NO:2, SEQ ID NO:3, SEQ ID NO:4, SEQ ID NO:5 and SEQ ID NO:6, wherein an at least 80% sequence identity between the two sequences indicates the presence of the virus in the biological sample.

13. An antibody that binds a polypeptide, wherein the polypeptide is encoded by a nucleic acid sequence which is comprised within the genome of the virus of claim 4, optionally wherein the polypeptide is selected from the group consisting of:

(i) a polypeptide comprising an amino acid sequence which is at least 80% identical to SEQ ID NO:7;

(ii) a polypeptide comprising an amino acid sequence which is at least 80% identical to SEQ ID NO:8;

(iii) a polypeptide comprising an amino acid sequence which is at least 80% identical to SEQ ID NO:9;

(iv) a polypeptide comprising an amino acid sequence which is at least 80% identical to SEQ ID NO:10; and (v) a polypeptide comprising an amino acid sequence which is at least 80% identical to SEQ ID NO:11.

14. A kit for detecting a virus in a biological sample from fish, wherein the kit comprises an oligonucleotide primer of claim 10, optionally wherein the kit is a real-time RT-PCR assay.

15. A viral polypeptide comprising an amino acid sequence that is at least 80% identical to any one of SEQ ID NOS 7-11.

16. The viral polypeptide according to claim 15, comprising an amino acid sequence that is at least 90% identical to any one of SEQ ID NOS 7-11.

17. The viral polypeptide according to claim 15, comprising an amino acid sequence that is at least 95% identical to any one of SEQ ID NOs 7-11.

18. The viral polypeptide according to claim 15, comprising an amino acid sequence comprising any one of SEQ ID NO: 7-11 or a conservatively substituted variant thereof.

19. The viral polypeptide according to claim 15, comprising an amino acid sequence comprising any one of SEQ ID NOS 7-11.

20. A vaccine comprising:

(i) a nucleic acid sequence as claimed in claim 1;

(ii) a viral polypeptide according to any claim 15; or (iii) a virus of claim 4.

21. The vaccine of claim 20, wherein the sequence of the nucleic acid is the sequence of the nucleic acid claimed in claim 1, wherein said nucleic acid sequence contains the base uracil (U) instead of the base thymine (T).

22. An interfering RNA (iRNA) molecule for use in treating fish infected with a virus, wherein the IRNA molecule comprises at least 12 consecutive nucleotides of, or complimentary to, a nucleic acid sequence comprised within the genome of the virus of claim 4.

* * * * *